US010085981B2

(12) United States Patent
Deschenes et al.

(10) Patent No.: US 10,085,981 B2
(45) Date of Patent: Oct. 2, 2018

(54) PROTEIN ACYL TRANSFERASE INHIBITORS AND METHODS OF TREATMENT

(71) Applicants: UNIVERSITY OF SOUTH FLORIDA, Tampa, FL (US); TORREY PINES INSTITUTE FOR MOLECULAR STUDIES, Port St. Lucie, FL (US)

(72) Inventors: Robert Joseph Deschenes, Tampa, FL (US); Marcello Angelo Giulianotti, Vero Beach, FL (US); Richard Allen Houghten, Port St. Lucie, FL (US); David Allen Mitchell, Lutz, FL (US); Laura Dawn Hamel, Temple Terrace, FL (US)

(73) Assignees: University of South Florida, Tamp, FL (US); Torrey Pines Institute for Molecular Studies, Port S. Lucie, FL (US)

( * ) Notice: Subject to any disclaimer, the term of this patent is extended or adjusted under 35 U.S.C. 154(b) by 0 days.

(21) Appl. No.: 15/744,399

(22) PCT Filed: Jul. 13, 2016

(86) PCT No.: PCT/US2016/042023
§ 371 (c)(1),
(2) Date: Jan. 12, 2018

(87) PCT Pub. No.: WO2017/011518
PCT Pub. Date: Jan. 19, 2017

(65) Prior Publication Data
US 2018/0200250 A1 Jul. 19, 2018

Related U.S. Application Data

(60) Provisional application No. 62/191,656, filed on Jul. 13, 2015.

(51) Int. Cl.
*A61K 31/496* (2006.01)
*A61P 35/02* (2006.01)

(52) U.S. Cl.
CPC ............ *A61K 31/496* (2013.01); *A61P 35/02* (2018.01)

(58) Field of Classification Search
CPC .............................. A61K 31/496; A61P 35/02
USPC ..................................................... 514/252.11
See application file for complete search history.

(56) References Cited

U.S. PATENT DOCUMENTS

2011/0041682 A1  2/2011  Makishima et al.
2012/0214798 A1  8/2012  Durrenberger et al.

OTHER PUBLICATIONS

International Search Report for PCT/US2016/042023 dated Oct. 7, 2016.
Nefzi et al. "Solid-Phase Synthesis of Bis-Heterocyclic Compounds from Resin-Bound Orthogonally Protected Lysine", J. Comb. Chem., 2001, vol. 3 (1), pp. 68-70.
Houghten et al. "Strategies for the Use of Mixture-Based Synthetic Combinatorial Libraries: Scaffold Ranking, Direct Testing In Vivo, and Enhanced Deconvolution by Computational Methods", J. Comb. Chem. 2008, vol. 10, pp. 3-19.
Kowalska et al. "Synthetic Small-Molecule Prohormone Convertase 2 Inhibitors", Molecular Pharmacology, 2009, vol. 75, No. 3, pp. 617-625.
2-bromopalmitate and 2-(2-hydroxy-5-nitro-benzylidene)-benzo[b]thiophen-3-one inhibit DHHC-mediated palmitoylation in vitro; Jennings, Benjamin C.; Nadolski, Marissa J.; Ling, Yiping; Baker, Meredith Beckham; Harrison, Marietta L.; Deschenes, Robert J.; Linder, Maurine E. Journal of Lipid Research (2009), 50, (2), 233-242.
Discovery and characterization of inhibitors of human palmitoyl acyltransferases; Ducker, Charles E.; Griffel, Lindsay. K.; Smith, Ryan A.; Keller, Staci N.; Zhuang, Yan; Xia, Zuping; Diller, John D.; Smith, Charles D. Molecular Cancer Therapeutics vol. 5 Issue7 pp. 1647-1659 Journal 2006.
Synthetic Inhibitors of Ras Palmitoylation: Defining a Novel Class of Drugs Targeting Breast Cancers, Blake R. Peterson, Sep. 2004 U.S. Army Medical Research and Materiel Command Fort Detrick, Maryland 21702-5012.
Chamberlain, L. H.Shipston, M. J. The physiology of protein S-acylation. Physiological reviews, 2015, 95, 341-76.
Rocks, O.;Peyker, A.;Kahms, M.;Verveer, P. J.;Koerner, C.;Lumbierres, M.;Kuhlmann, J.;Waldmann, H.;Wittinghofer, A.Bastiaens, P. I. An acylation cycle regulates localization and activity of palmitoylated Ras isoforms. Science, 2005, 307, 1746-52.
Mitchell, D. A.; Mitchell, G.;Ling, Y.;Budde, C.Deschenes, R. J. Mutational analysis of Saccharomyces cerevisiae Erf2 reveals a two-step reaction mechanism for protein palmitoylation by DHHC enzymes. J Biol Chem, 2010, 285, 38104-14.
Jennings, B. C.;Linder, M. E. DHHC protein S-acyltransferases use similar ping-pong kinetic mechanisms but display different acyl-CoA specificities. J Biol Chem, 2012, 287, 7236-45.
Ohno, Y.;Kihara, A.;Sano, T.Igarashi, Y. Intracellular localization and tissue-specific distribution of human and yeast DHHC cysteine-rich domain-containing proteins. Biochimica et biophysica acta, 2006, 1761, 474-83.
Roth, A. F.;Wan, J.;Bailey, a. O.;Sun, B.;Kuchar, J. A.;Green, W. N.;Phinney, B. S.;Yates, J. R., 3rdDavis, N. G. Global analysis of protein palmitoylation in yeast. Cell, 2006, 125, 1003-13.
Yeste-Velasco, M.;Linder, M. E.Lu, Y. J. Protein S-palmitoylation and cancer. Biochimica et biophysica acta, 2015, 1856, 107-120.
Webb, Y.;Hermida-Matsumoto, L.Resh, M. D. Inhibition of protein palmitoylation, raft localization, and T cell signaling by 2-bromopalmitate and polyunsaturated fatty acids. J Biol Chem, 2000, 275, 261-70.

(Continued)

*Primary Examiner* — Yevgeny Valenrod
(74) *Attorney, Agent, or Firm* — Thomas | Horstemeyer, LLP

(57) ABSTRACT

Embodiments of the present disclosure include compositions and pharmaceutical compositions that include protein acyl transferases (PAT) inhibitors, methods of treating a condition or disease, methods of treating autopalmitoylation activity, and the like.

16 Claims, 13 Drawing Sheets

(56) References Cited

OTHER PUBLICATIONS

Davda, D.;Ei Azzouny, M. A.;Tom, C. T.;Hernandez, J. L.;Majmudar, J. D.;Kennedy, R. T.Martin, B. R. Profiling targets of the irreversible palmitoylation inhibitor 2-bromopalmitate. ACS chemical biology, 2013, 8, 1912-7.

Pedro, M. P.;Vilcaes, A. A.;Tomatis, V. M.;Oliveira, R. G.;Gomez, G. A.Daniotti, J. L. 2-Bromopalmitate reduces protein deacylation by inhibition of acyl-protein thioesterase enzymatic activities. PlOS one, 2013, 8, e75232, 1-11.

Houghten, R. A.;Pinilla, C.;Giulianotti, M. A.;Appel, J. R.;Dooley, C. T.;Nefzi, A.;Ostresh, J. M.;Yu, Y.;Maggiora, G. M.; Medina-Franco, J. L.;Brunner, D.Schneider, J. Strategies for the use of mixture-based synthetic combinatorial libraries: scaffold ranking, direct testing in vivo, and enhanced deconvolution by computational methods. J Comb Chem, 2008, 10, 3-19.

Santos, R. G.;Appel, J. R.;Giulianotti, M. A.;Edwards, B. S.;Sklar, L. A.;Houghten, R. A.Pinilla, C. The mathematics of a successful deconvolution: a quantitative assessment of mixture-based combinatorial libraries screened against two formylpeptide receptors. Molecules, 2013, 18, 6408-24.

Hamel, L. D.;Deschenes, R. J.Mitchell, D. A. A Fluorescence-Based Assay to Monitor Autopalmitoylation of zDHHC Proteins Applicable to High Throughput Screening. Analytical biochemistry, 2014, 1-8.

Ito, H.;Fukada, Y.;Murata, K.Kimura, A. Transformation of intact yeast cells treated with alkali cations. J.Bacteriol., 1983, vol. 153, No. 1, 163-168.

Bartels, D. J.;Mitchell, D. A.;Dong, X.Deschenes, R. J. Erf2, a novel gene product that affects the localization and palmitoylation of Ras2 in *Saccharomyces cerevisiae.* Mol Cell Biol, 1999, vol. 19, No. 10, 6775-87.

Ostresh, J. M.;Winkle, J. H.;Hamashin, V. T.Houghten, R. A. Peptide libraries: determination of relative reaction rates of protected amino acids in competitive couplings. Biopolymers, 1994, 34, 1681-9.

Houghten, R. A.;Pinilla, C.;Appel, J. R.;Blondelle, S. E.;Dooley, C. T.;Eichler, J.;Nefzi, A.Ostresh, J. M. Mixture-based synthetic combinatorial libraries. J Med Chem, 1999, 42, 3743-78.

Pinilla, C.;Appel, J. R.;Blanc, P.Houghten, R. A. Rapid identification of high affinity peptide ligands using positional scanning synthetic peptide combinatorial libraries. Biotechniques, 1992, 13, 901-5.

Acharya, A. N.;Ostresh, J. M.Houghten, R. A. Determination of isokinetic ratios necessary for equimolar incorporation of carboxylic acids in the solid-phase synthesis of mixture-based combinatorial libraries. Biopolymers, 2002, 65, 32-9.

Santos, R. G.;Giulianotti, M. A.;Dooley, C. T.;Pinilla, C.;Appel, J. R.Houghten, R. A. Use and implications of the harmonic mean model on mixtures for basic research and drug discovery. ACS combinatorial science, 2011, 13, 337-44.

Santos, R. G.;Giulianotti, M. A.;Houghten, R. A.Medina-Franco, J. L. Conditional probabilistic analysis for prediction of the activity landscape and relative compound activities. J Chem Inf Model, 2013, 53, 2613-25.

Minond, D.;Cudic, M.;Bionda, N.;Giulianotti, M.;Maida, L.;Houghten, R. A.Fields, G. B. Discovery of novel inhibitors of a disintegrin and metalloprotease 17 (ADAM17) using glycosylated and non-glycosylated substrates. J Biol Chem, 2012, 287, 36473-87.

Reilley, K. J.;Giulianotti, M.;Dooley, C. T.;Nefzi, A.;McLaughlin, J. P.Houghten, R. A. Identification of two novel, potent, low-liability antinociceptive compounds from the direct in vivo screening of a large mixture-based combinatorial library. The AAPS journal, 2010, 12, 318-29.

Wu, J.;Zhang, Y.;Maida, L. E.;Santos, R. G.;Welmaker, G. S.;LaVoi, T. M.;Nefzi, A.;Yu, Y.;Houghten, R. A.;Toll, L. Giulianotti, M. A. Scaffold ranking and positional scanning utilized in the discovery of nAChR-selective compounds suitable for optimization studies. J Med Chem, 2013, 56, 10103-17.

Mitchell, D. A.;Hamel, L. D.;Ishizuka, K.;Mitchell, G.;Schaefer, L. M.Deschenes, R. J. The Erf4 subunit of the yeast Ras palmitoyl acyltransferase is required for stability of the Acyl-Erf2 intermediate and palmitoyl transfer to a Ras2 substrate. J Biol Chem, 2012, 287, 34337-48.

Mansilla, F.;Birkenkamp-Demtroder, K.;Kruhoffer, M.;Sorensen, F. B.;Andersen, C. L.;Laiho, P.;Aaltonen, L. A.; Verspaget, H. W.Orntoft, T. F. Differential expression of DHHC9 in microsatellite stable and instable human colorectal cancer subgroups. British journal of cancer, 2007, 96, 1896-903.

Cuiffo, B.Ren, R. Palmitoylation of oncogenic NRAS is essential for leukemogenesis. Blood, 2010, 115, 17, 3598-3605.

Choi, Y. W.;Bae, S. M.;Kim, Y. W.;Lee, H. N.;Park, T. C.;Ro, D. Y.;Shin, J. C.;Shin, S. J.;Seo, J. S.Ahn, W. S. Gene expression profiles in squamous cell cervical carcinoma using array-based comparative genomic hybridization analysis. Int J Gynecol Cancer, 2007, 17, 687-96.

Oyama, T.;Miyoshi, Y.;Koyama, K.;Nakagawa, H.;Yamori, T.;Ito, T.;Matsuda, H.;Arakawa, H.Nakamura, Y. Isolation of a novel gene on 8p21.3-22 whose expression is reduced significantly in human colorectal cancers with liver metastasis. Genes, Chromosomes & Cancer, 2000, 29, 9-15.

De Vos, M. L.;Lawrence, D. S.Smith, C. D. Cellular pharmacology of cerulenin analogs that inhibit protein Biochemical palmitoylation pharmacology, 2001, 62, 985-95.

Draper, J. M.Smith, C. D. Palmitoyl acyltransferase assays and inhibitors (Review). Mol Membr Biol, 2009, 26, 5-13.

Omura, S. The antibiotic cerulenin, a novel tool for biochemistry as an inhibitor of fatty acid synthesis. Bacteriol Rev, 1976, 40, 681-97.

Patterson, S. I.Skene, J. H. Inhibition of dynamic protein palmitoylation in intact cells with tunicamycin. Methods Enzymol, 1995, 250, 284-300.

Schlag, B. D.;Lou, Z.;Fennell, M.Dunlop, J. Ligand dependency of 5-hydroxytryptamine 2C receptor internalization. J Pharmacol Exp Ther, 2004, 310, 865-70.

Christopher, J. A.;Brown, J.;Dore, A. S.;Errey, J. C.;Koglin, M.;Marshall, F. H.;Myszka, D. G.;Rich, R. L.;Tate, C. G.; Tehan, B.;Warne, T.Congreve, M. Biophysical fragment screening of the beta1-adrenergic receptor: identification of high affinity arylpiperazine leads using structure-based drug design. J Med Chem, 2013, 56, 3446-55.

Debevec, G.;Chen, W.;Yu, Y.;Houghten, R. A.Giulianotti, M. A. Libraries from Libraries: A Series of Sulfonamide Linked Heterocycles Derived from the Same Scaffold. Tetrahedron letters, 2013, 54, 4296-4299.

a) 5% DIEA/DCM; b) Fmoc-Lys(Boc)-OH, DIC, HOBt, DMF; c) 20% Piperidine/DMF; d) R1COOH, DIC, HOBt, DMF; e) 55% TFA/DCM; f) Boc-AA(R2), DIC, HOBt, DMF] g) R3COOH, DIC, HOBt, DMF; h) BH#-THF, 65°C, 96 hours; i) Piperidine, 65°C, 24 hours; j) Oxalydiimidazole, DMF; k) HF, anisole, 0°C

PROTEIN ACYL TRANSFERASE INHIBITORS AND METHODS OF TREATMENT

CROSS-REFERENCE TO RELATED APPLICATIONS

This application is the 35 U.S.C. § 371 national stage application of PCT Application No. PCT/US2016/042023, filed Jul. 13, 2016, where the PCT claims the benefit of and priority to U.S. Provisional Application Ser. No. 62/191,656, having the title "PROTEIN ACYL TRANSFERASE INHIBITORS," filed on Jul. 13, 2015, both of which are herein incorporated by reference in their entireties.

STATEMENT REGARDING FEDERALLY SPONSORED RESEARCH OR DEVELOPMENT

This invention was made with government support under contracts R01 CA050211 and R01 GM007397 awarded by the National Institutes of health. The government has certain rights in the invention.

BACKGROUND

S-acylation is the enzymatic addition of a fatty acid (acyl) group onto one or more cysteine residues of a protein via a thioester linkage. The bulk of S-acylation involves the addition of a C16:0 carbon palmitoyl moiety and so we will refer to S-acylation as S-palmitoylation. Alterations in palmitoylation have been implicated in the etiology of cancer, cardiovascular disease, and neurological disorders. Thus, there is a need to address alterations in palmitoylation.

SUMMARY

Embodiments of the present disclosure include compositions and pharmaceutical compositions that include protein acyl transferases (PAT) inhibitors, methods of treating a condition or disease, methods of treating autopalmitoylation activity, and the like.

An embodiment of the present disclosure includes a composition, among others, that includes a compound having the following structure:

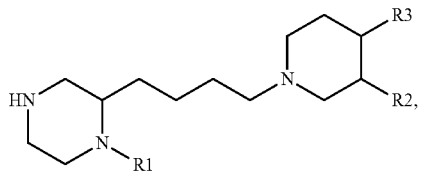

wherein each of R1, R2, and R3 is independently selected from the group consisting of:

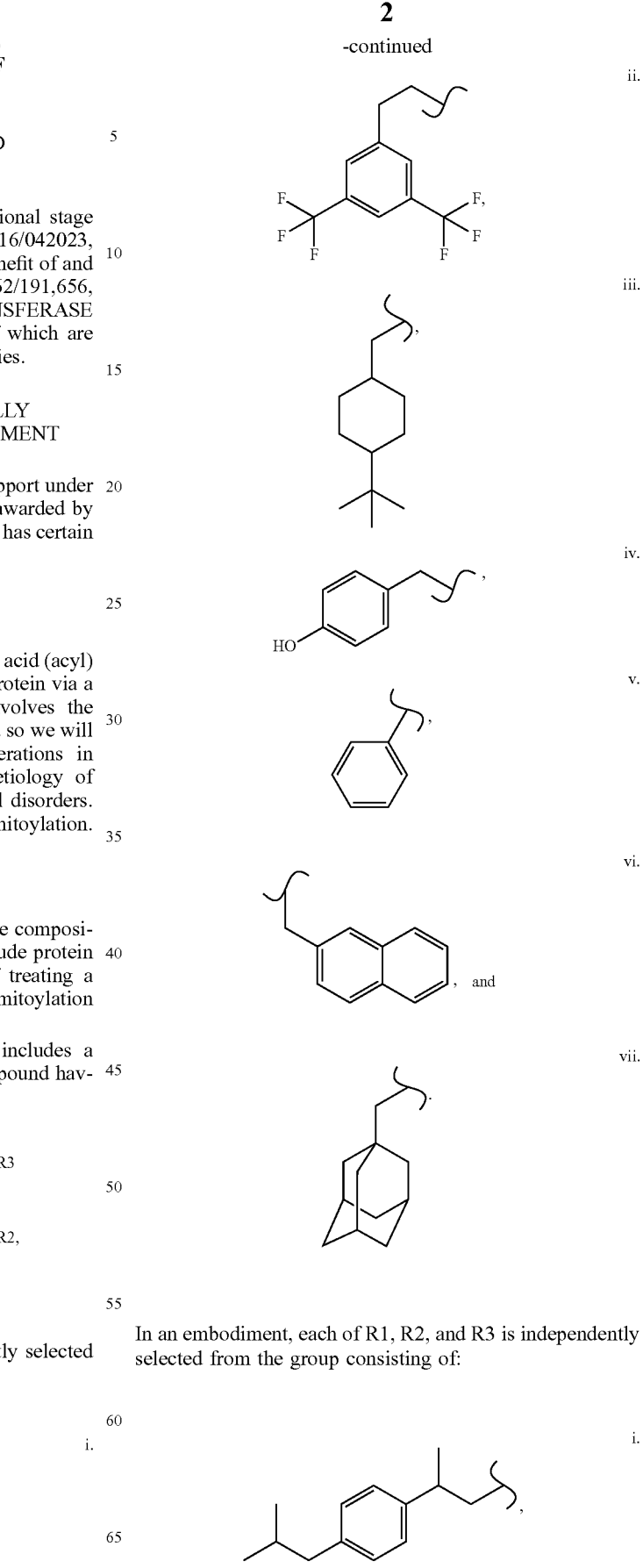

In an embodiment, each of R1, R2, and R3 is independently selected from the group consisting of:

-continued

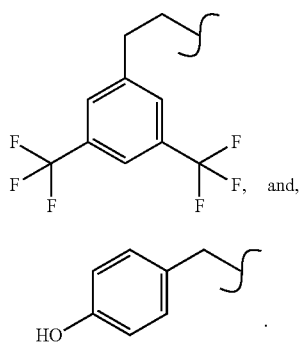

In an embodiment, R1 is

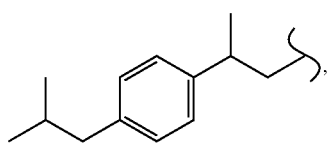

R2 is

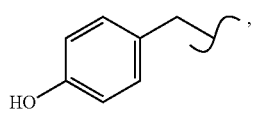

and R3 is

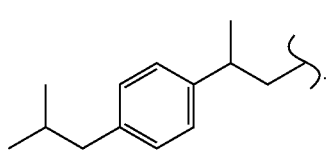

In an embodiment, R1 is

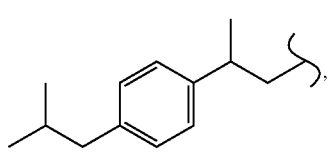

R2 is

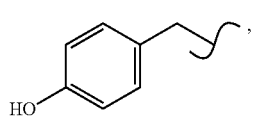

and R3 is

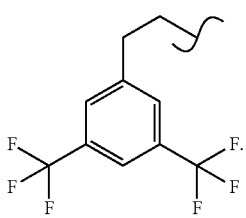

In an embodiment, R1 is

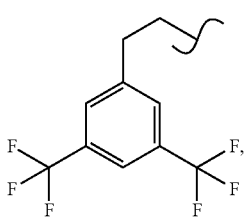

R2 is

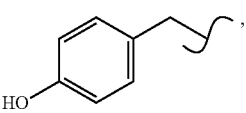

and R3 is

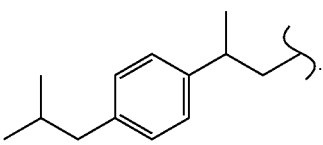

An embodiment of the present disclosure includes a pharmaceutical composition, among others, that includes a therapeutically effective amount of a compound, or a pharmaceutically acceptable salt of the compound, and a pharmaceutically acceptable carrier, to treat a condition, wherein the compound has a structure as described herein such as those described above. In an embodiment, the condition can be a disease such as: colorectal cancer, leukemia, and cervical cancer.

An embodiment of the present disclosure includes a method of treating autopalmitoylation activity, among others, that includes a delivering to a subject in need thereof, a pharmaceutical composition, wherein the pharmaceutical composition includes a therapeutically effective amount of a compound, or a pharmaceutically acceptable salt of the compound, and a pharmaceutically acceptable carrier, wherein the compound has a structure as described herein such as those described above.

An embodiment of the present disclosure includes a method of treating a disease, among others, that includes delivering to a subject in need thereof, a pharmaceutical composition, wherein the pharmaceutical composition includes a therapeutically effective amount of a compound, or a pharmaceutically acceptable salt of the compound, and a pharmaceutically acceptable carrier, wherein the disease is selected from the group consisting of: colorectal cancer, leukemia, and cervical cancer, wherein the compound has a structure as described herein such as those described above.

Other compositions, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 3A shows the velocity of Erf2 autopalmitoylation on the coupled assay with the lead scaffold ranking library samples (2160, 2220, 2236, 2221, 2103). The velocity of Erf2 auto-palmitoylation was detected as an increase in fluorescence over time. Average values of three reactions are presented as a fraction of vehicle control (1% DMF) +/−standard deviation. Samples were screened at 50 µg/ml (dark grey bars), 100 µg/ml (light grey bars), and 200 µg/ml (white bars) compared to 2-BP at 50 µM (dark grey bars), 100 µM (light grey bars), and 200 µM (white bars). A reaction lacking Erf2 (−) represents baseline activity in the assay. B, Structures of lead scaffolds and 2-Bromopalmitic Acid. Positions for varying functional groups are denoted by R1-R4. Scaffold 2160 contains three R-group positions, scaffolds 2220, 2221, and 2103 each contain two R-group positions, and scaffold 2236 contains four R-group positions.

DETAILED DESCRIPTION

Figure 1:
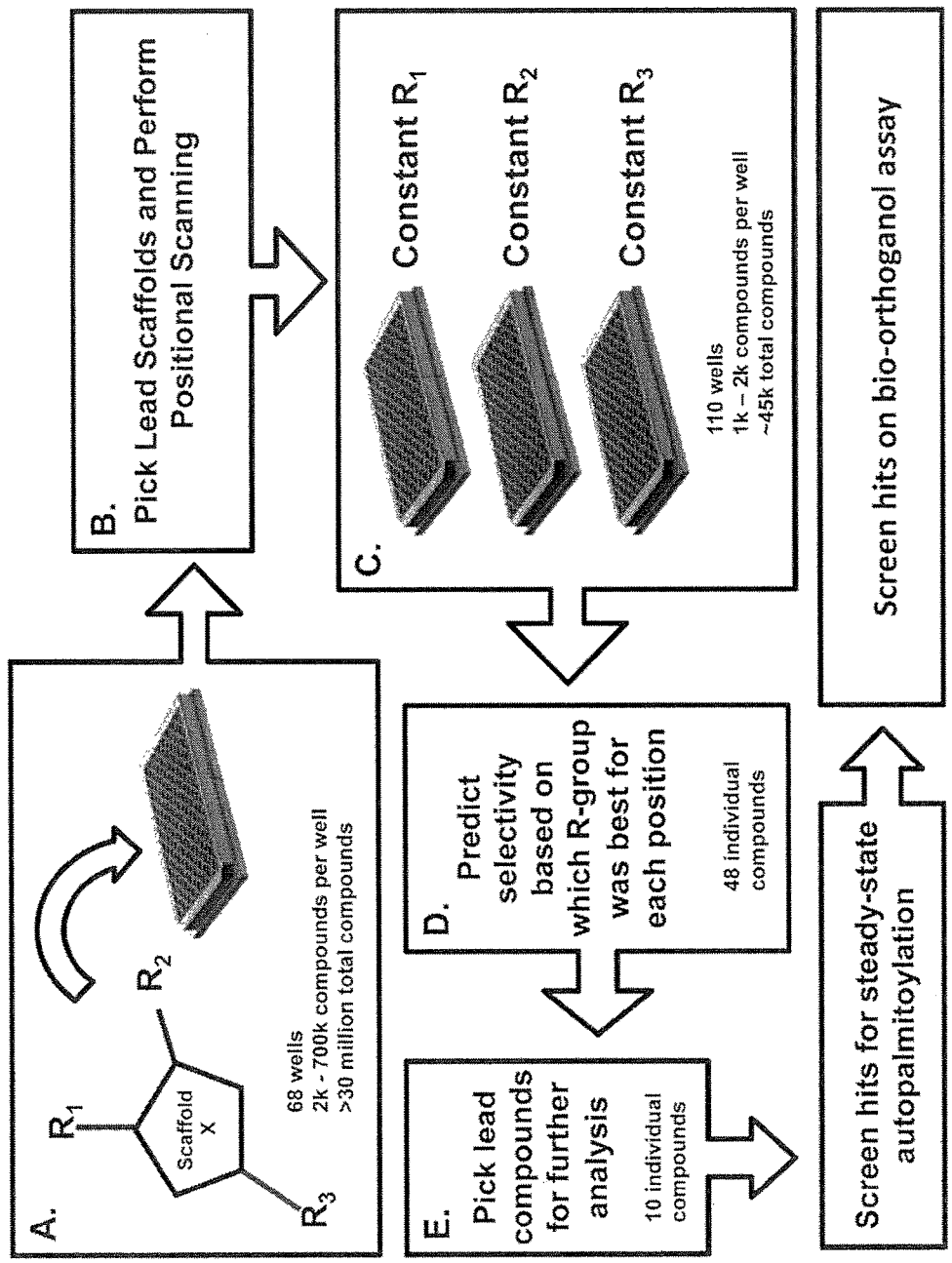
FIG. 1 is a schematic representation of the chemical library screen. In stage A, the Torrey Pines Institute for Molecular Studies scaffold library approach starts with >30 million compounds that are organized by 68 core scaffolds with 2,000-700,000 different compounds per scaffold. In stage B, a lead scaffold is selected for the positional scanning screen. In stage C, all of the compounds in the positional scanning screen contain the same core scaffold structure and are organized by the R-groups at each position. Each of the plates contains the same compounds organized by the different R-group position to determine if a particular functional group is optimal at one of the positions. The positional scanning library screened in this study contained 110 positional scanning samples that each comprise of 1,000-2,000 individual compounds for a total diversity of 45864 individual compounds. In stage D, the selectivity for the different R-groups is predicted for each position based on the positional scanning results. In this study, 48 individual compounds were synthesized. In stage E, of the 48 individual compounds synthesized ten were selected for further analysis in additional assays. In total, 226 samples were tested: 68 Scaffolds, 110 positional scanning scaffolds, and 48 individual compounds.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biology, chemistry, material science, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

Unless otherwise defined, all technical and scientific terms used herein have the same meaning as commonly understood by one of ordinary skill in the art of molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "unit dosage form," as used herein, refers to physically discrete units suitable as unitary dosages for human and/or animal subjects, each unit containing a predetermined quantity of a compound (e.g., compositions or pharmaceutical compositions, as described herein (e.g., PAT inhibitor)) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the subject.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition (e.g., PAT inhibitor) being administered that will relieve to some extent one or more of the symptoms of the disease, i.e., cancer, leukemia, and the like, being treated, and/or that amount that will prevent, to some extent, one or more of the symptoms of the disease that the subject being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition (e.g., PAT inhibitor) form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure (e.g., PAT inhibitor) that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure (e.g., PAT inhibitor) that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure (e.g., PAT inhibitor), and salts thereof, may exist in their tautomeric form, all such tautomeric forms are contemplated herein as part of the present disclosure.

All stereoisomers of the compounds of the composition or pharmaceutical composition of the present disclosure (e.g., PAT inhibitor), such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure (e.g., PAT inhibitor) that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365, Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a composition of the present disclosure (e.g., PAT inhibitor) into a subject. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition (e.g., cancer, leukemia, and the like), a disease or a disorder with a composition (e.g., PAT inhibitor) to affect the condition, disease or disorder by improving or altering it. The improvement or alteration may include an improvement in symptoms or an alteration in the physiologic pathways associated with the condition, disease, or disorder. "Treatment," as used herein, covers one or more treatments of a condition or a disease in a subject (e.g., a mammal, typically a human or non-human animal of veterinary interest), and includes: (a) reducing the risk of occurrence of the condition, or a disease in a subject determined to be predisposed to the condition or disease but not yet diagnosed with it (b) impeding the development of the disease, and/or (c) relieving the disease, e.g., causing regression of the disease and/or relieving one or more disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition, a disease, or a symptom thereof and/or may be therapeutic in terms of a partial or complete cure for a disease, and/or adverse effect attributable to the disease.

As used herein, the term "subject," or "patient," includes humans, mammals (e.g., mice, rats, pigs, cats, dogs, and horses), and birds. Typical subjects to which compounds of the present disclosure (e.g., PAT inhibitor) may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

Abbreviations:

CoA, Coenzyme A; PAT, protein acyl transferase; HTS, high throughput screen; APT, acyl protein thioesterase; DMF, dimethylformamide; 2-BP, 2-bromopalmitic acid; DIEA, diisopropylethylamine; MBHA, p-methylbenzyhydrylamine; DCM, dichloromethane; DIC, diisopropylcarbodiide; HOBt, 1-hydroxybenzotriazole hydrate; TFA, trifluoroacetic acid; THF, tetrahydrofuran; MEOH, methanol.

General Discussion

Embodiments of the present disclosure include compositions and pharmaceutical compositions that include protein acyl transferases (PAT) inhibitors, methods of treating a condition or disease, methods of treating autopalmitoylation activity, and the like. Embodiments of the present disclosure include a PAT inhibitor that includes a bis-cyclic piperazine scaffold, where the PAT inhibitor inhibits autopalmitoylation activity, specifically Erf2 autopalmitoylation, and can be used to treat diseases. In particular, dysregulation of protein palmitoylation has been linked to a number of diseases including colorectal cancer, cervical cancer, and leukemia, as a result embodiments of the present disclosure can be used to treat these diseases.

In an embodiment, the composition and pharmaceutical composition can include a PAT inhibitor. In an embodiment, the PAT inhibitor can have the following structure:

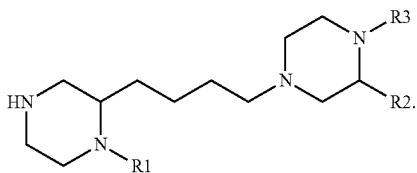

Optionally, each of the H on the carbons in the rings and/or alkyl chain can be substituted with a halogen. In an embodiment, each of R1, R2, and R3 can be independently:

i.
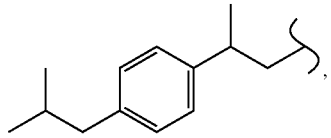

ii.
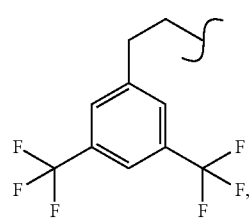

iii.
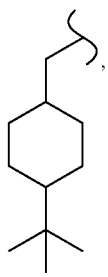

iv.
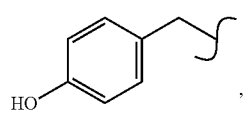

v.
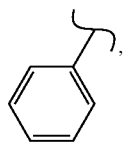

vi.
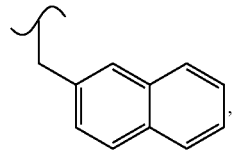

and vii.
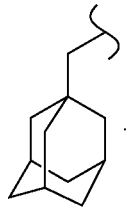

Optionally, each of the H on the carbons in the rings and/or alkyl chain can be substituted with a halogen, and for moiety II, one or more of the F groups can be substituted with another halogen or H. In a particular embodiment, each of R1, R2, and R3 can be independently:

i.
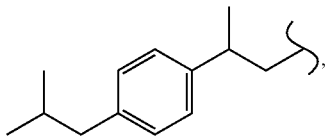

ii.
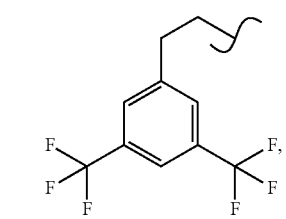

and, iv.
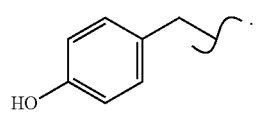

In a particular embodiment, where R1 can i.
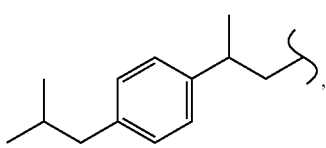

R2 is iv.
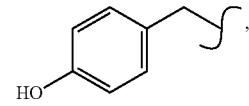

and R3 is i.
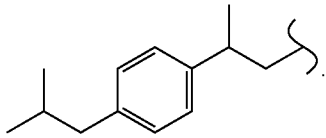

In a particular embodiment, where R1 is i.
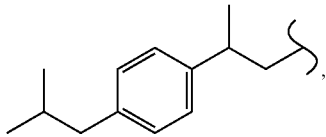

R2 is iv. 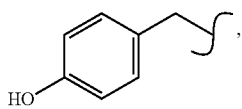

and R3 is ii. 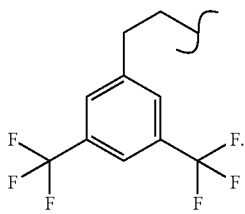

In a particular embodiment, where R1 is ii. 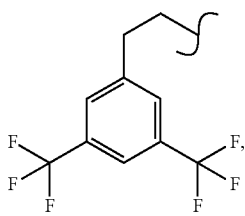

R2 is iv. 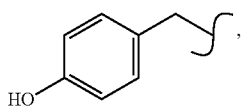

and R3 is i. 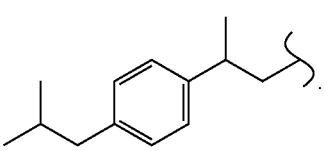

Additional details are provided in Example 1.

As it relates to the pharmaceutical composition, the pharmaceutical composition can include a therapeutically effective amount of the compound, or a pharmaceutically acceptable salt of the compound, and a pharmaceutically acceptable carrier, to treat a condition. In an embodiment, the condition can be a disease such as cancer (e.g., colorectal cancer, cervical cancer) or leukemia (e.g., leukemogenesis). Additional details regarding the pharmaceutical composition are provided herein.

Embodiments of this disclosure include methods of treating a subject using the composition or the pharmaceutical composition described herein for a condition or disease (e.g., cancer) and methods of treating autopalmitoylation activity using the composition or the pharmaceutical composition described herein. Additional details regarding the pharmaceutical composition are provided herein.

In a particular embodiment, the composition or the pharmaceutical composition including the PAT inhibitor can be used to treat a disease in a subject. For example, the composition or the pharmaceutical composition is provided or administered to a subject in an amount effective to result in uptake of the PAT inhibitor. In an embodiment, the steps of this method can be repeated at determined intervals to treat the disease. In this embodiment, the treatment can be provided periodically (e.g., daily, weekly, monthly, intervals in between these, and the like).

It should be noted that the amount effective to result in uptake of the PAT inhibitor may depend upon a variety of factors, including for example, the age, body weight, general health, sex, and diet of the host; the time of administration; the route of administration; the rate of excretion of the specific probe employed; the duration of the treatment; the existence of other drugs used in combination or coincidental with the specific composition employed; and like factors well known in the medical arts.

Pharmaceutical Formulations and Routes of Administration

Embodiments of the present disclosure include a compound (e.g., PAT inhibitor) as identified herein and formulated with one or more pharmaceutically acceptable excipients, diluents, carriers and/or adjuvants. In addition, embodiments of the present disclosure include a compound formulated with one or more pharmaceutically acceptable auxiliary substances. In particular the compound can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins, and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the compound can be administered to the subject using any means capable of resulting in the desired effect. Thus, the compound can be incorporated into a variety of formulations for therapeutic administration. For example, the compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the compound may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the compound can be utilized in aerosol formulation to be administered via inhalation. Embodiments of the compound can be formulated into pressurized acceptable propellants such as dichlorodifluoromethane, propane, nitrogen and the like.

Furthermore, embodiments of the compound can be made into suppositories by mixing with a variety of bases such as emulsifying bases or water-soluble bases. Embodiments of the compound can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the compound in a composition as a solution in sterile water, normal saline or another pharmaceutically acceptable carrier.

Embodiments of the compound can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles in accordance with the present disclosure.

In an embodiment, the compound can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the compound can be accomplished using any of a variety of refillable, pump systems. Pumps provide consistent, controlled release over time. In some embodiments, the compound can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., POT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., compounds A-D) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109;

6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the compound are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the compound may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the compound (e.g., PAT inhibitor) can be administered to a subject in one or more doses. Those of skill will readily appreciate that dose levels can vary as a function of the specific the compound administered, the severity of the symptoms and the susceptibility of the subject to side effects. Preferred dosages for a given compound are readily determinable by those of skill in the art by a variety of means.

In an embodiment, multiple doses of the compound are administered. The frequency of administration of the compound can vary depending on any of a variety of factors, e.g., severity of the symptoms, and the like. For example, in an embodiment, the compound can be administered once per month, twice per month, three times per month, every other week (qow), once per week (qw), twice per week (biw), three times per week (tiw), four times per week, five times per week, six times per week, every other day (god), daily (qd), twice a day (qid), or three times a day (tid). As discussed above, in an embodiment, the compound is administered continuously.

The duration of administration of the compound analogue, e.g., the period of time over which the compound is administered, can vary, depending on any of a variety of factors, e.g., patient response, etc. For example, the compound, in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the compound (e.g., PAT inhibitor) to a subject (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the compound) can be administered in a single dose or in multiple doses.

Embodiments of the compound can be administered to a subject using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the compound. Where systemic delivery is desired, administration typically involves invasive or systemically absorbed topical or mucosal administration of pharmaceutical preparations.

In an embodiment, the compound can also be delivered to the subject by enteral administration. Enteral routes of administration include, but are not limited to, oral and rectal (e.g., using a suppository) delivery.

Methods of administration of the compound through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

We have recently described a high-throughput screening technique for quantifying autopalmitoylation and will be applying that assay to a screening campaign for inhibitors of palmitoylation from a unique compound scaffolding chemical library. This approach allows for the interrogation of millions of compounds with only hundreds of reactions [11-13]. In the present disclosure, we describe the use of this assay for the identification of a unique class of compounds, based on a bis-cyclic piperazine scaffold that inhibits the autopalmitoylation activity of the yeast Ras PAT, Erf2.

S-acylation is the enzymatic addition of a fatty acid (acyl) group onto one or more cysteine residues of a protein via a thioester linkage. The bulk of S-acylation involves the addition of a C16:0 carbon palmitoyl moiety and so we will refer to S-acylation as S-palmitoylation. A number of cellular processes involve the regulated addition of palmitate to proteins and includes signal transduction, protein turnover, vesicle fusion, and cell-cell interactions. At the protein level, the addition of palmitate enhances a protein's membrane affinity as well as distribution in membrane micro-domains, mediates protein-protein interactions, trafficking, stability, and aggregation state [1]. While other protein lipidations, such as prenylation and myristoylation, are physiologically irreversible, the formation of the thioester linkage indicative of protein palmitoylation is reversible, and has led to a proposal that repeated rounds of acylation and de-acylation regulate substrate activity, localization and turn-over [2].

A family of protein acyl transferases (PATs) catalyzes the addition of a palmitoyl moiety to proteins. Genes encoding members of the PAT family have been identified in all sequenced eukaryotic genomes. This family of enzymes catalyze palmitoylation by a two-step reaction [3-6]. The first step, autopalmitoylation, results in the formation of the enzyme-palmitoyl intermediate via a thioester linkage between palmitate, donated from palmitoyl-CoA, and the active site cysteine of the enzyme. The palmitoyl moiety is then transferred from the enzyme to a receiver cysteine of the protein substrate in the second step of the reaction. In the absence of a protein substrate, water attacks the active site causing hydrolysis of the enzyme-palmitoyl complex thioester linkage, thus regenerating the enzyme and producing palmitic acid [3, 4].

Alterations in palmitoylation have been implicated in the etiology of cancer, cardiovascular disease, and neurological disorders [1, 7]. However, there are currently no drugs that target palmitoylation and the limited numbers of inhibitors that do exist exhibit low affinity and lack specificity. The most widely used inhibitor, 2-bromopalmitic acid (2-BP), is a non-metabolizable palmitate analog that elicits pleiotropic effects on cellular metabolism [8]. Despite a recent mass spectrometry study where its preference for palmitoylated substrates or PAT enzymes was not detectable, 2-BP continues to be the primary experimental inhibitor of palmitoylation in part due to the lack of a more suitable alternative [9]. Furthermore, 2-BP also inhibits the depalmitoylating thioesterase, Apt1 [10]. Thus, the need to identify specific, high affinity inhibitors of protein palmitoylation is critical for the progression of palmitoylation research, and for the regulation of palmitoylation for therapeutic intervention.

Materials and Methods

Strains, Media, and Yeast Techniques

Yeast growth media were prepared as described previously [14]. Cells were grown in synthetic complete (SC) medium or YPD (1% yeast extract, 2% peptone, and 2% glucose) medium [14]. Induction of GAL1, 10 promoters were achieved by adding 4% galactose to SC medium in the absence of glucose. Yeast transformations were performed using the lithium acetate procedure [15]. Three yeast strains were used for this study: RJY1941 (S288C) MATα leu2-3,112 ura3-52 ade2 ade8 lys2 ras1::HIS3 Ras2(CS-ext) erf2Δ::KAN$^r$ erg6Δ::TRP1 [YCp52-RAS2], RJY1942 (S288C) MATα leu2-3,112 ura3-52 ade2 ade8 lys2 ras1::HIS3 Ras2 (CS-ext) erf2Δ::KAN$^r$ erg6Δ:TRP1 [YCp52] and RJY1842 (MATa/α ade2-1/ade2-1 leu2-3,112/leu2-3,112 ura3-52/ura3-52 trp1-1/trp1-1 his3-11,15/his3-11,15 can1-100/can1-100 GAL$^+$/GAL$^+$ psi$^+$/psi$^+$ erf4Δ::NAT$^r$/erf4Δ::NAT$^r$ [16].

Protein Purification

Strain RJY1842 was transformed with pESC(-Leu)-6×HIS-Erf2-(Flag)-Erf4 and grown to 2×10$^7$ cells/ml in SC(-Leu) medium containing 2% (v/v) ethanol/2% (v/v) glycerol at 30° C. with shaking. 50 mls (1×10$^9$ cells) were added to 1 liter of YEP medium supplemented with 4% galactose for induction. Cells were induced with shaking (230 RPM) for 18 hrs (30° C.) and then harvested by centrifugation at 3000×g for 15 mins. The resulting pellet was resuspended in breaking buffer (50 mM Tris-CI pH 8, 500 ml NaCl, 1 mM EDTA, 1 mM DTT, 1×PIC, 8 μl/ml saturated PMSF/isopropyl alcohol), and the cells were lysed using glass beads (400-600 mesh, Sigma) for 40 mins with 1 min pulses (1 min cooling). The resulting extract was spun at 3000×g for 15 mins to remove cellular debris and unbroken cells, followed by a crude membrane fraction (P13) by centrifugation (13,000×g) for 0.5 hrs at 4° C. The supernatant was discarded and the pellet was resuspended in Tris buffered saline, pH 8, with the aid of a Dounce homogenizer. The resulting extract was adjusted to a final concentration of 1% Triton-X100. To solubilize the membranes, the extract was incubated at 4° C. (1.5 hrs). Insoluble material was then removed by centrifugation (13,000×g) for 0.5 hrs at 4° C. The supernatant was incubated with Ni-NTA resin at 4° C. for 1 hr. The resin was washed 3× with Solution W (50 mM Tris-CI, pH 8, 150 mM NaCl and 1% Triton-X100). The protein was eluted with 50 mM Tris-CI, pH 8, 150 mM NaCl, 1% Triton-X100, 5% glycerol and 250 mM imidazole. Eluates were desalted and concentrated using 50 mM Tris-CI, pH 8, 150 mM NaCl, 1% Triton-X100 and 5% glycerol. Fractions containing 6×His-Erf2-(FLAG)-Erf4 were pooled to obtain approximately 0.2 mg of purified Ras PAT per liter of culture as determined by SDS-PAGE against a standard curve of bovine serum albumin. The complexes were divided into 50 μL aliquots and frozen at −80° C. until use.

Coupled PAT Assay

The HTS application of protein palmitoylation was recently described [13], but was adjusted for this study. The production of NADH was monitored with a Biotek Mx fluorimeter (Biotek, Winooski, Vt.) using 340 nm excitation/ 465 nm emission. The 50 µl reaction contained 2 mM 2-Oxoglutarate (α-ketoglutamic acid), 0.25 mM NAD+, 0.2 mM Thiamine Pyrophosphate, 0.5 µg of purified 6×HIS-Erf2-(FLAG)-Erf4, 1 mM EDTA, 1 mM dithiothreitol, 8 mU 2-oxogluarate dehydrogenase (α-ketoglutarate dehydrogenase), 50 mM sodium phosphate, pH 6.8, and 0 100 µM inhibitor in 5% DMF. The reaction was initiated by the addition of 40 µM palmitoyl-CoA and monitored for 30 mins at 30° C. The first 10 mins of the reaction was analyzed to determine the initial rates of CoASH release. The PAT specific activity was determined from a standard curve of NADH production with different CoASH amounts. In these reactions, CoASH was added to the standard PAT reaction mixture (without Erf2/Erf4 complex or palmitoyl-CoA) and the reaction was allowed to proceed to equilibrium before fluorescence was measured.

Scaffold Ranking Library

The scaffold ranking library contains one sample for each of the 68 positional scanning libraries tested. Each of these samples contains an approximate equal molar amount of each compound in that library. So, for example, the sample 2160 in the scaffold ranking library contains 45,864 compounds in approximately equal molar amounts. These samples can be prepared by mixing the cleaved products of the complete positional scanning library, as was the case for sample 2160, or they can be synthesized directly as a single mixture [12, 17]. Refer to Supplemental Material section below for a thorough description of the synthesis of the scaffold ranking library and subsequent individual compounds.

Positional Scanning Library 2160

The positional scanning library incorporates both individual and mixtures of amino acids (R2) and carboxylic acid (R1 and R3). The synthetic technique facilitates the generation of information regarding the likely activity of individual compounds from the screening of the library [11, 18, 19]. Equimolar isokinetic ratios have been previously determined and calculated for each of the amino and carboxylic acids utilized for the respective mixtures [17, 20]. The bispiperazine library 2160 has a total diversity of 45,864 compounds (42×26×42=45,864). The R1 and R3 positions each have 42 carboxylic acids and the R2 position contains 26 amino acids.

BODIPY®-C12:0 Autopalmitoylation Assay

BODIPY®-C12:0-CoA (40 µM final, unless specified otherwise) was added to a 50 µl reaction containing approximately 0.5 µg enzyme (6×HIS-Erf2-(FLAG)-Erf4) and 100 µM inhibitors in 5% DMF in 50 mM sodium phosphate buffer, pH 6.8. The reactions were incubated 10 mins with inhibitor, and then the reaction was initiated with the addition of BODIPY®-C12:0-CoA, and incubated 15 mins at 30° C. The reaction was terminated by the addition of 5× non-reducing protein loading buffer. Each reaction was heated at 65° C. for 3 mins and then subjected to SDS-PAGE (12%). The gel was rinsed three times in ddH2O and visualized on the Typhoon 9410 Variable Mode Imager (GE Healthcare, Piscataway, N.J.) for BODIPY® fluorescence (ex. 488 nm/em. 532 nm) to visualize co-migration of the BODIPY® signal with 6×HIS-Erf2-(FLAG)-Erf4. The amount of 6×HIS-Erf2-(FLAG)-Erf4 was determined empirically using SDS-PAGE analysis under reducing conditions against a standard curve of bovine serum albumin.

Growth Inhibition Assay

The in vivo effect of the inhibitors on Ras2 palmitoylation was investigated by comparing the growth of S. cerevisiae strains previously described for our complementation assay [16]. Briefly, the cells contain a defective allele of RAS2 that is balanced by an episomal copy of RAS2 linked to URA3. Under these conditions, the yeast strain cannot grow unless the episomal copy of RAS2 is palmitoylated. Varying concentrations of the inhibitors were added to 200 µl volumes of the yeast cells at an $OD_{600}$ between 0.8 and 1.2 in a 96-well plate format. The $OD_{600}$ was observed every 30 mins for 24 hrs and $EC_{50}$ values were determined by graphing rate of growth against concentration of inhibitor for each inhibitor.

Yeast Cell Spot Assay

Following 24 hrs incubation with varying concentrations of the inhibitors in 1% DMF, S. cerevisiae strains RJY1941 and RJY1942 were then diluted 1/100, and spotted onto SC-Ura plates with 2% glucose. Cytotoxicity data was obtained by detecting the colony growth, following 48 hrs incubation at 30° C., with white light detection on the Bio-Rad Molecular Imager® ChemiDoc™ XRS+ (Hercules, Calif.) and performing densitometry with Bio-Rad ImageLab™ Software (Hercules, Calif.). Triplicate reactions were plated in triplicate. Values were normalized to vehicle control (1% DMF) for each plate, and then the averages of each reaction were compared for statistical analysis.

Results

Inhibition of Erf2 Autopalmitoylation Using a Fluorescence-Based Coupled Assay

The identification of palmitoylation inhibitors has been hampered by the lack of assays amenable to high throughput screening applications. Previously, we validated an assay that monitors the rate of autopalmitoylation by measuring the production of CoASH generated from the reduction of palmitoyl-CoA [13]. This assay has a Z'-value of 0.87 [13]. The intention of this assay is to couple the amount of CoASH formed (and hence, enzyme:palmitoyl intermediate formed) to the production of NADH, which is fluorescent. This assay can be used to monitor autopalmitoylation in real time or as an end point assay, thus providing flexibility when screening small molecule compounds. Compounds with internal fluorescence or that affect the assay components are easily identified and excluded, allowing for the rapid identification of the compounds that inhibit or activate PAT autopalmitoylation activity.

As an initial step in our screening campaign, we interrogated a scaffold ranking library developed by the Torrey Pines Institute for Molecular Studies [11-13]. This strategy allows for the evaluation of >30 million synthetic compounds while screening exponentially fewer reactions. This is achieved by organizing a large number of chemically diverse compounds into 68 core scaffolds. Each scaffold contains between 2,000 to 700,000 unique compounds at approximately equal molar concentrations. It is predicted that structural similarities will dictate additive effects increasing the chance that individual modulators will be detected despite being between nanomolar to sub-nanomolar concentrations [12, 21]. The vast number of structurally similar compounds in each scaffold library sample increases the probability of identifying a compound with useful chemical characteristics and properties [22]. FIG. 1 highlights a flow diagram of the stages involved in the identification and optimization of the compounds. We first screened the 68 scaffolds to determine the optimal scaffold structure (FIG. 1, stage A). Once identified, positional scanning libraries of the lead scaffolds, which are organized by R-groups at each position around a given scaffold, are screened (FIG. 1, stage B). This allows for the prediction of optimal R-groups for each position on the core scaffold (FIG. 1, stage C). Based on the optimized scaffold and knowledge of the active R-groups, individual compounds can be designed and synthesized to determine the positional effects of the R-groups on activity (FIG. 1, stage D). Finally, based on the level of inhibition, we selected a subset of lead compounds for further analysis (FIG. 1, stage E). This approach allows us to expedite the screening process of millions of compounds and to generate structure activity relationship (SAR) information earlier in the screening process. A description of the library construction and use can be found in recent reviews [11, 22-25].

Scaffold Ranking of the Erf2 Autopalmitoylation Inhibitors

Figure 2:
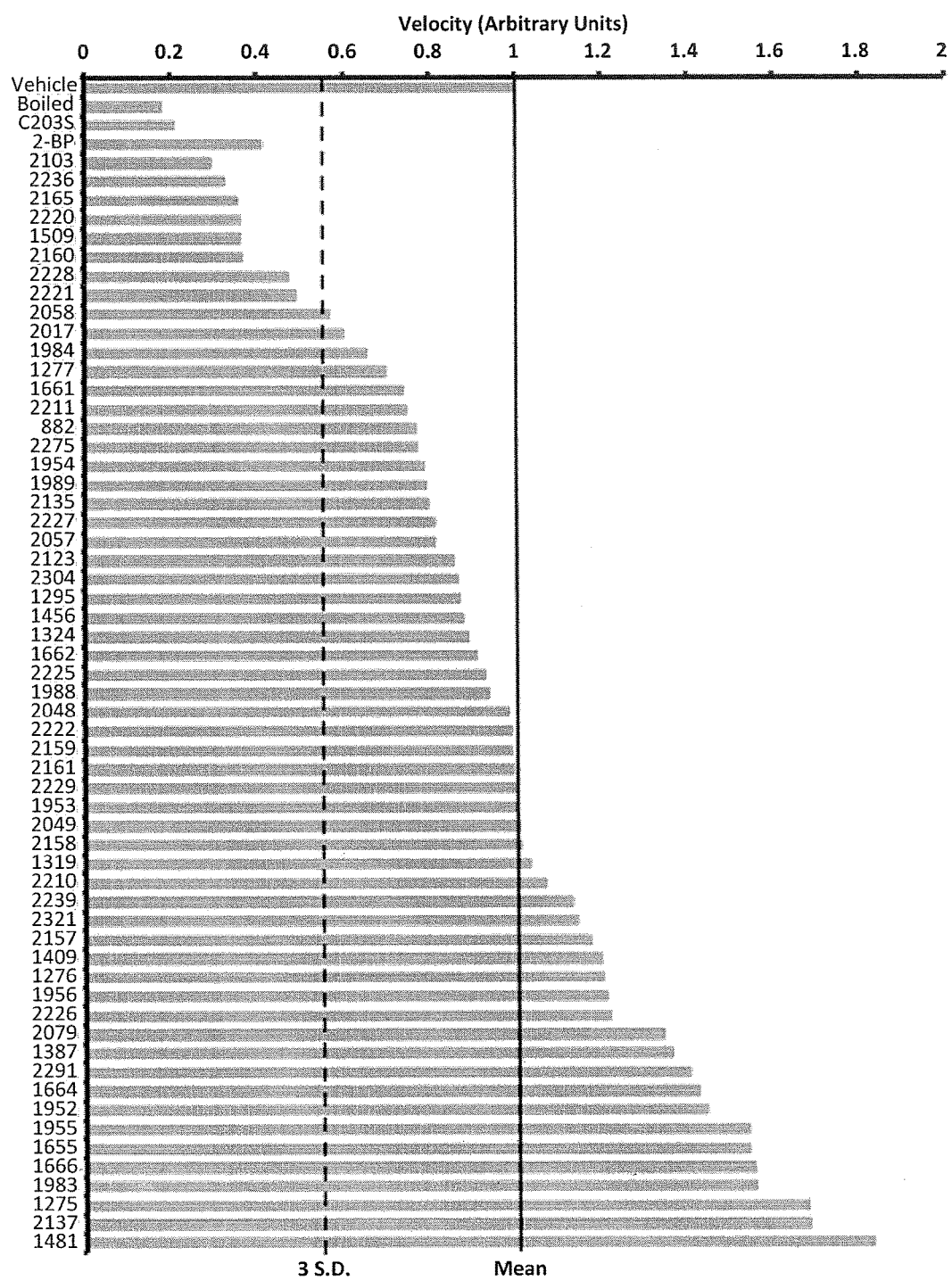
FIG. 2 illustrates the results of the screen for inhibition of Erf2 auto-palmitoylation. The scaffold ranking library screen of 68 scaffolds was screened at 100 µg/ml, and the average velocity of Erf2 auto-palmitoylation of three reactions is presented as a fraction of vehicle control (1% DMF). The velocity of Erf2 auto-palmitoylation was detected as an increase in fluorescence over time. No effect on Erf2 auto-palmitoylation would fall at 1 arbitrary unit (solid line). Scaffolds that resulted in a reduction in Erf2 auto-palmitoylation 3 standard deviations (dashed line) or greater were considered hits of this assay. A heat inactivated Erf2 (Boiled) and a catalytically inactive mutant of Erf2 (C203S) represent baseline activity in this assay. 100 µM 2-BP is a control for inhibition of Erf2 auto-palmitoylation.

We screened 68 scaffold ranking samples, each at a concentration of 100 µg/ml/scaffold (FIG. 2). Each scaffold sample was pre-incubated with Erf2 enzyme for 10 mins at 30° C. before initiating the reaction with the addition of palmitoyl-CoA. We monitored the production of CoASH for 30 mins to ensure a linear response over time and determined the rate of the reaction for each scaffold sample. Incubation of the enzyme with several of the scaffold samples resulted in a reduction in the production of CoASH. As an initial criterion, we defined inhibition as a reduction in activity greater than three standard deviations from the mean activity value. We identified eight of the scaffold libraries that fit this definition. Scaffolds 2103, 2236, 2165, 2220, 1509, 2160, 2228, and 2221 caused at least a 50% reduction in Erf2 autopalmitoylation activity. In contrast, scaffold 1509 appeared to react with the assay components and was excluded from further analysis. The data from two of the scaffolds, 2165 and 2228, were not reproducible and these scaffolds were also excluded (data not shown). We established a baseline of inhibition using boiled and catalytically inactive enzyme.

Figure 3A:
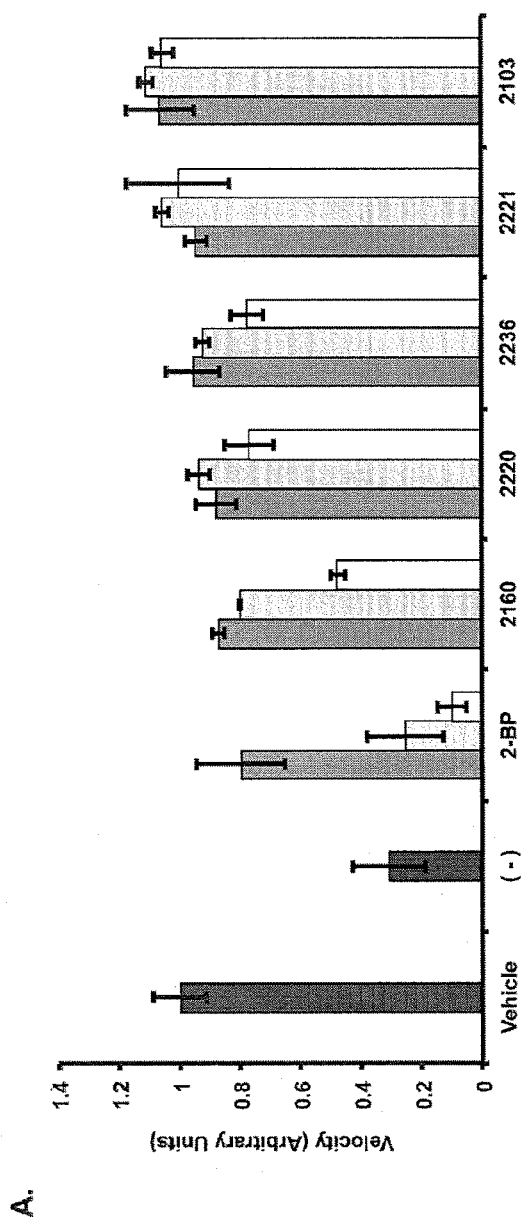
FIGS. 3A-B show inhibition of Erf2 auto-palmitoylation by varying the concentration of library samples.
Figure 3B:
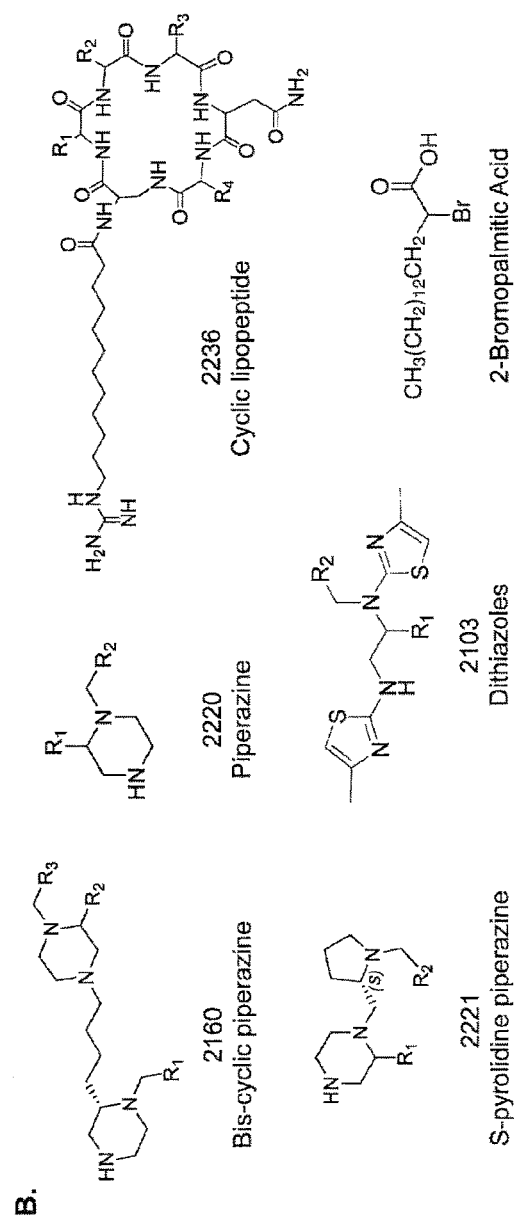

The remaining 5 scaffolds were then screened for dose responsiveness at 200 µg/ml, 100 µg/ml, and 50 µg/ml (FIG. 3A). Similar to the dosage response observed for 2-BP, three of the five scaffold libraries (2160, 2220 and 2236) demonstrated some degree of dosage response at these concentrations. Interestingly, these three scaffold libraries included a piperazine-analog feature. Scaffold 2220 is a piperazine, scaffold 2221 is a pyrolidine piperazine, and scaffold 2160 is a bis-cyclic piperazine (FIG. 3B). Of these, scaffold 2160 reproducibly decreased PAT activity in a dose dependent fashion to the greatest extent. Structurally, scaffold 2160 has a core bis-cyclic piperazine with three R-groups, and a total diversity of 45864 compounds (FIG. 1B).

The 45864 compounds in scaffold 2160 were synthesized into 110 mixture samples organized by R-group (FIG. 1, stage C). At position R1 and R3 there were 42 functionalities derived from different carboxylic acids (samples 2160.001-2160.042 and 2160.069-2160.110, respectively), and 26 derived from amino acids at the R2 position (samples 2160.043-2160.068). Thus, samples organized by R1 or R3 positions contain 1092 (42×26) compounds per sample, and samples organized by the R2 position contain 1764 (42×42) compounds per sample. The 110 samples were screened for inhibition of Erf2 autopalmitoylation at a concentration of 100 µg/ml. Ninety-nine of the 110 mixture samples had no significant effect on Erf2 autopalmitoylation, where 25% inhibition was considered the cutoff for significance (data not shown). Four functional groups at position R1, three at position R2 and four at position R3, resulted in a greater than 25% reduction and were selected for synthesis of 48 individual compounds.

Individual Compounds Screened for Inhibition of Erf2 Autopalmitoylation

Figure 4:
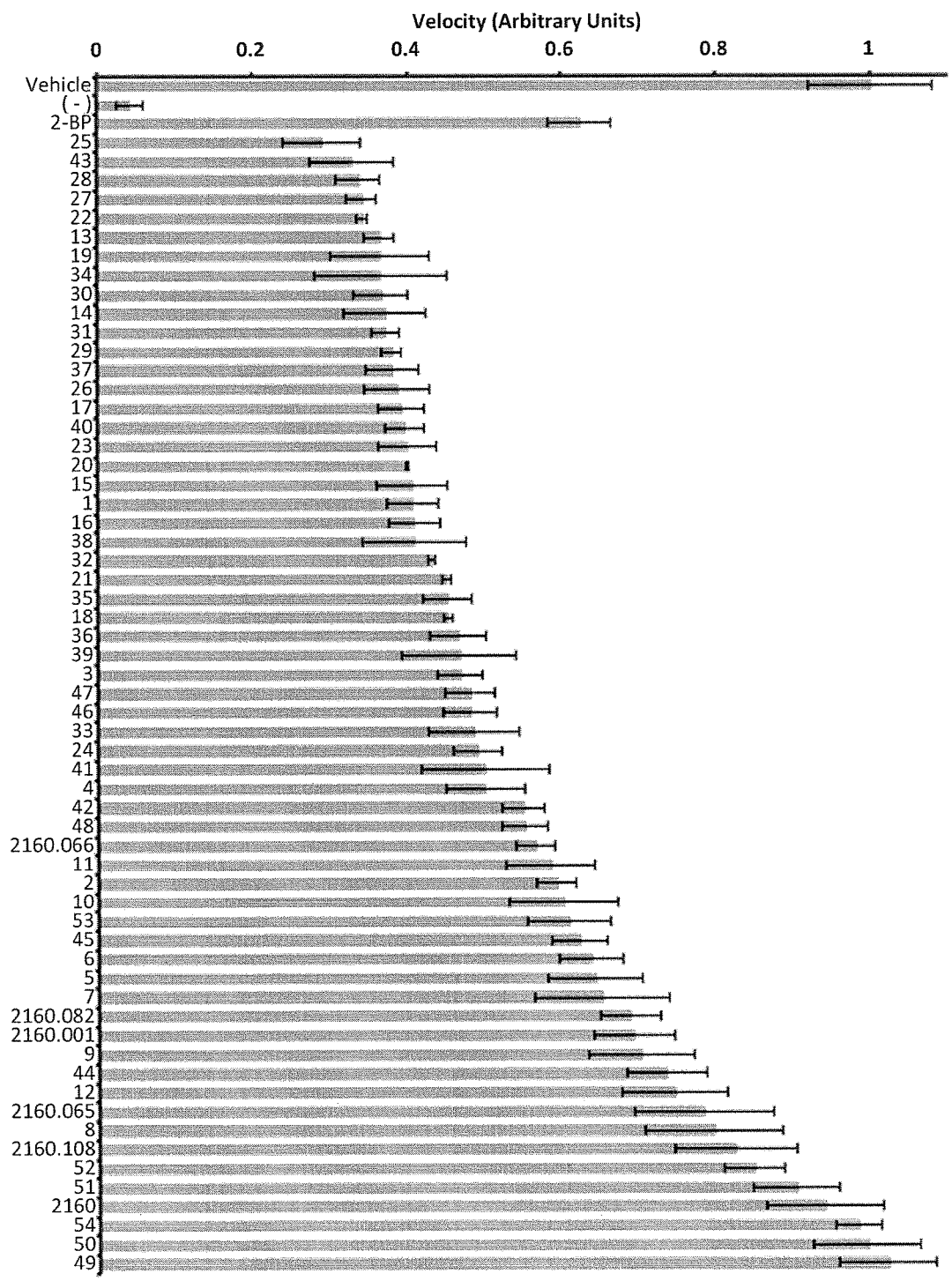
FIG. 4 graphs inhibition of Erf2 auto-palmitoylation by individual compounds derived from the 2160 scaffold. Relative velocity of Erf2 auto-palmitoylation with 100 µg/ml of optimized individual compounds (1-48), non-specific individual compounds (49-54), positional scanning samples (2160.066, 2160.082, 2160.001, 2160.065, and 2160.108), and lead scaffold ranking library sample (2160). The velocity of Erf2 auto-palmitoylation was detected as an increase in fluorescence over time. Average values of three reactions presented as a fraction of vehicle control (1% DMF) +/−standard deviation. A reaction lacking Erf2 (−) represents baseline activity in the assay. 50 µM 2-BP is a control for inhibition of Erf2 auto-palmitoylation.

The 48 compounds were screened with five of the hits from the positional scanning samples (2160.066, 2160.082, 2160.001, 2160.065, and 2160.108) and the complete 2160-scaffold sample (FIG. 4). Scaffold 2160 and the positional scanning samples inhibited Erf2 autopalmitoylation consistent with prior screens and demonstrated that as the complexity decreased from 45864 compounds (scaffold 2160), to 1000-2000 compounds (positional scanning), and finally, to individual compounds, there was a concomitant increase in the inhibition of Erf2 autopalmitoylation (FIG. 4). As an additional control, we included non-optimized compounds (compounds 49-54), which were designed with side groups that did not pass the original cutoff in the positional scanning screen. These compounds, as anticipated, demonstrated poor inhibition of Erf2 autopalmitoylation in comparison to the compounds whose design was based on the positional scanning results. We determined the inhibition constant (K) for the top ten compounds by determining the rate of autopalmitoylation activity for varying amounts of inhibitor compound (data not shown). The autopalmitoylation inhibition constants ranged from ~63-142 µM for the ten compounds identified in this study, and 59 µM for 2-BP (FIG. 5, right panel).

Figure 5:
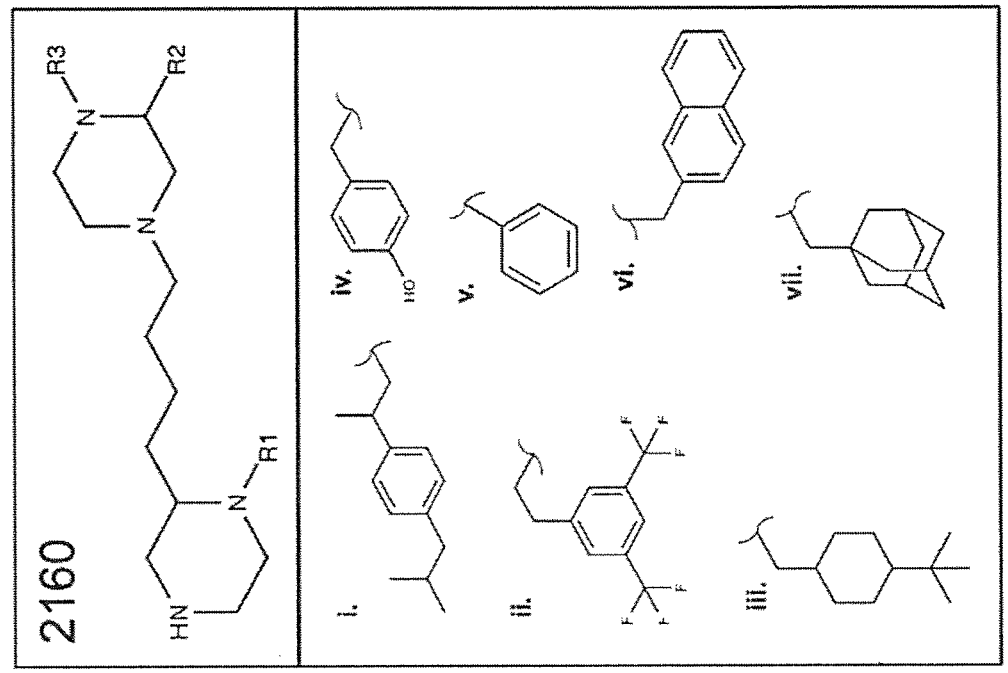
FIG. 5 shows the structure of the scaffold 2160 derived compounds. The structure for scaffold 2160, bis-cyclic piperazine has three R-group positions designated R1, R2, and R3. The lead functional groups are 2-(4-Isobutyl-phenyl)-propyl (i), 2-(3,5-bis-trifluoromethyl-phenyl)ethyl (ii), 4-tert-butyl-cyclohexyl-methyl (iii), S-4-hydroxybenzyl (iv), S-phenyl (v), S-2-naphthylmethyl (vi), and adamantan-1-yl-methyl (vii). The curved lines on the functional group structures designate where they will share a bond with the core scaffold. Positions for each functional group are described in the right panel. $K_i$ values for the fluorescence-based coupled assay of the rate of Erf2 autopalmitoylation (FCA) and the orthogonal gel-based assay of steady-state Erf2 autopalmitoylation (GBA) are listed for each compound (14, 13, 25, 28, 34, 19, 22, 43, 27, and 30) as well as $EC_{50}$ values obtained from the growth curve experiments in S. cerevisiae RJY1942 (Sens.) and RJY1941 (cont.). All values are represented in µM concentrations. The increased detection sensitivity of the FCA allowed for the determination of standard deviation.

There did not appear to be a preference within the top 40 compounds for the R2 position amongst the four possibilities; hydroxybenzyl, phenyl, and (S or R) naphthylmethyl groups (FIG. 5). There were three possibilities at the R3 position, and it was at this position that the greatest preference was observed. 2-(4-isobutyl-phenyl)-propyl was the optimal group at this position and is present in seven of the top ten hits. 2-(3,5-bis-trifluoromethyl-phenyl)-ethyl is the most prevalent in the next 15, and the completely aliphatic functional group, adamantan-1-yl-methyl, is in this position for a majority of the remaining top 40 individual compounds. The R1 position also showed similar specificity for the functional groups utilized in the individual compounds. At the R1 position, nearly all of the top 30 compounds have either 2-(3,5-bis-trifluoromethylphenyl)-ethyl or 2-(4-isobutyl-phenyl)-propyl, the same top two groups for the R3 position. A >50% reduction in Erf2 autopalmitoylation was observed for most of the optimized individual compounds, but only the top ten were selected for additional analysis.

Figure 6:
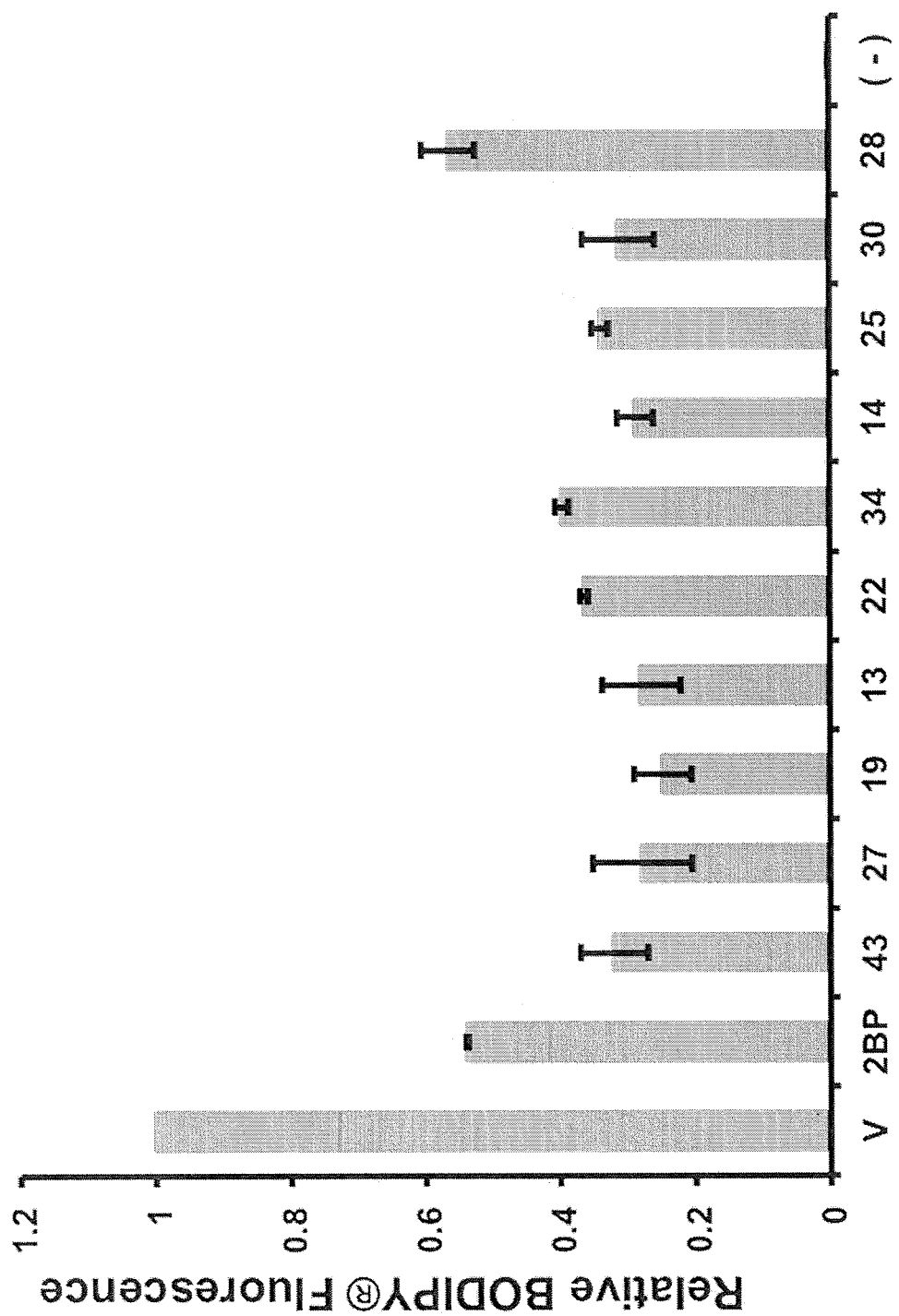
FIG. 6 shows inhibition of Erf2 auto-palmitoylation measured by a gel-based assay. An orthogonal screen of steady-state Erf2 autopalmitoylation with 100 µM of each of the ten individual compounds (43, 27, 19, 13, 22, 34, 14, 25, 30, and 28) was separated by SDS-PAGE. The average relative BODIPY® fluorescence from three reactions that co-migrated with Erf2 is presented as a fraction of vehicle control (V; 5% DMF) +/−standard deviation. A reaction lacking Erf2 (−) represents baseline activity in the assay. 100 µM 2-BP is a control for inhibition of Erf2 steady-state auto-palmitoylation.

To determine if the ten compounds identified in this study were inhibiting autopalmitoylation, and not targeting hydrolysis of the enzyme, steady-state autopalmitoylation was evaluated at 100 µM of each compound compared to 100 µM 2-BP and DMF (vehicle) alone. This was performed in a gel-based reaction using BODIPY®-C12-CoA [26]. The reactions were separated by SDS-PAGE and steady-state autopalmitoylation was determined by the relative BODIPY® fluorophore that co-migrated with Erf2, demonstrating that Erf2 was acylated by BODIPY®-012 [26]. At 100 µM, the ten compounds each resulted in a 50% or greater decrease in steady-state Erf2 autopalmitoylation compared to vehicle alone. From these screens we observed a decrease in BODIPY® fluorescence at the apparent molecular weight of Erf2. This does not confirm that the inhibitors are directly interacting with Erf2 as they could be reducing the stability of the Erf2-Erf4 complex. Taking that into consideration, all of the compounds inhibited autopalmitoylation to either an equal or greater extent compared to 2-BP (FIG. 6). Dose response curves of steady-state autopalmitoylation activity were examined to determine the $K_i$ for each compound (data not shown). The steady-state autopalmitoylation inhibition constants ranged from ~34-72

μM for the ten compounds identified in this study, and 79 μM for 2-BP (FIG. 5, right panel).

Compounds 13 and 25 Competitively Inhibit Erf2 Autopalmitoylation

The potential for the symmetry of the compounds to play a role in their efficacy is of interest as the same functional groups were identified for the top two leads at both positions R1 and R3, and positions R1 and R3 are located on nitrogens of the opposing piperazine ring structures on the bis-cyclic piperazine scaffold. To interrogate this, the compounds 13, 14, and 25 were selected for further analysis as they represent a unique set of three compounds where all three have the same functional group at position R1, compound 13 has the lead functional group, 2-(3,5-bis-trifluoromethyl-phenyl)-ethyl, at positions R1 and R3, compound 14 also has 2-(3,5-bis-trifluoromethyl-phenyl)-ethyl at position R1, but has the second lead functional group, 4-tert-butyl-cyclohexyl-methyl at the R3 position, and compound 25 has the reverse; 4-tert-butylcyclohexyl-methyl at the R1 position and 2-(3,5-bis-trifluoromethyl-phenyl)-ethyl at position R3. Thus, compound 13 represents a compound with symmetry and compounds 14 and 25 are complementary non-symmetrical representatives with the same alternative functional group at opposite positions. Of the ten lead compounds, these three are the only ones to satisfy this scenario.

Figure 7:
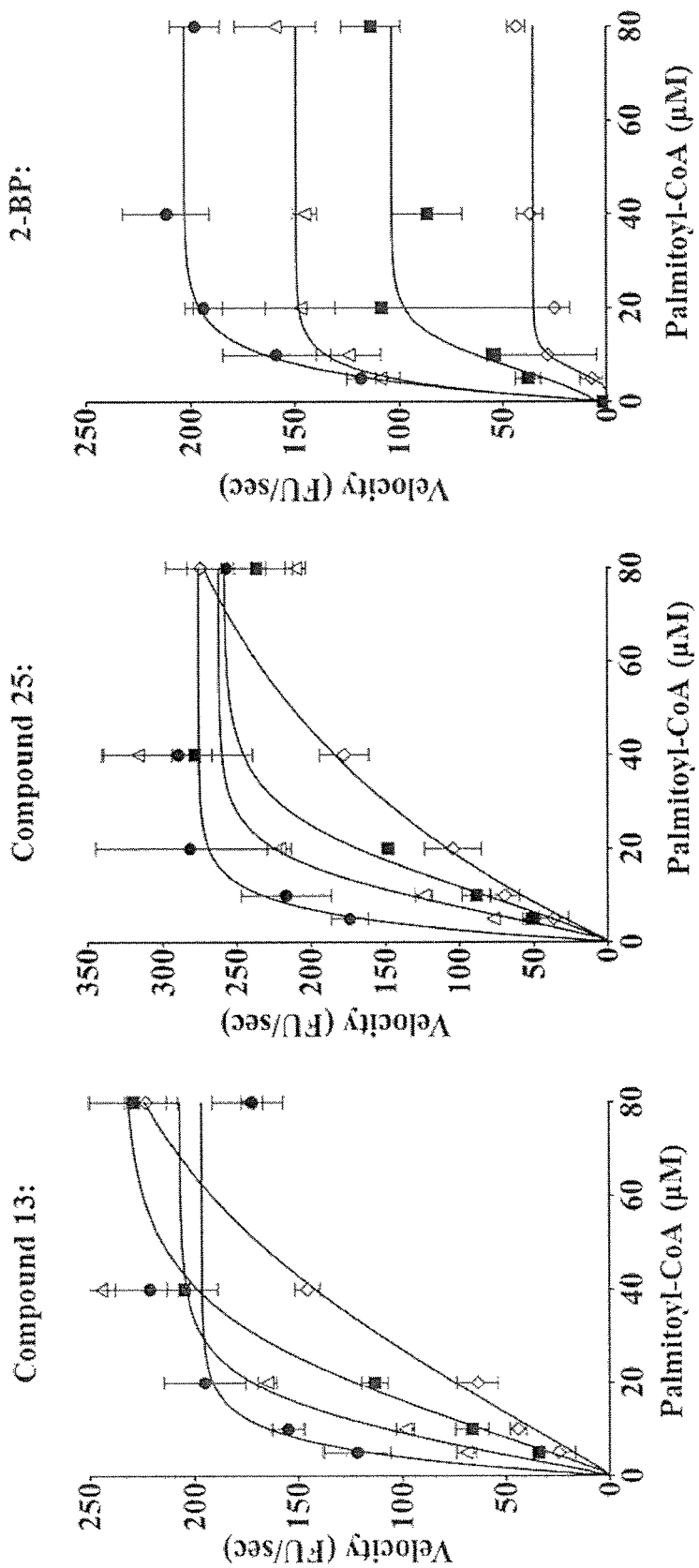
FIG. 7 provides Michaelis-Menten plots for Compounds 13 and 25, and 2-BP. The velocity of Erf2 auto-palmitoylation as altered by the addition of the inhibitors at 100 µM (empty diamonds), 50 µM (filled squares), 25 µM (empty triangles), and vehicle control (1% DMF; filled circles) for compounds 13 and 25, and 2-BP. The velocity of Erf2 auto-palmitoylation was detected as an increase in fluorescence over time. $V_{MAX}$ is the maximum velocity of the reaction, and $K_M$ is the substrate concentration that allows the reaction to reach a velocity that is 50% of the $V_{MAX}$. On the Michaelis-Menton Plot, a competitive inhibitor would increase $K_M$ without altering $V_{MAX}$, whereas an uncompetitive inhibitor would result in a decrease of $V_{MAX}$ without altering the $K_M$ of the reaction.

To first elucidate if these compounds were mechanistically different from 2-BP, we performed inhibitor titrations, varying the amount of compound 13 (or compound 25) and palmitoyl-CoA. Over the concentration range tested, compounds 13 and 25, increasing inhibitor concentration increased the $K_M$ (palmitoyl-CoA) of the reaction while having little effect on the $V_{MAX}$. (FIG. 7). It was not possible to increase palmitoyl-CoA concentrations above 80 μM due to the CMC. The $K_M$ and Vow values calculated are summarized in Table 1.

Figure 8:
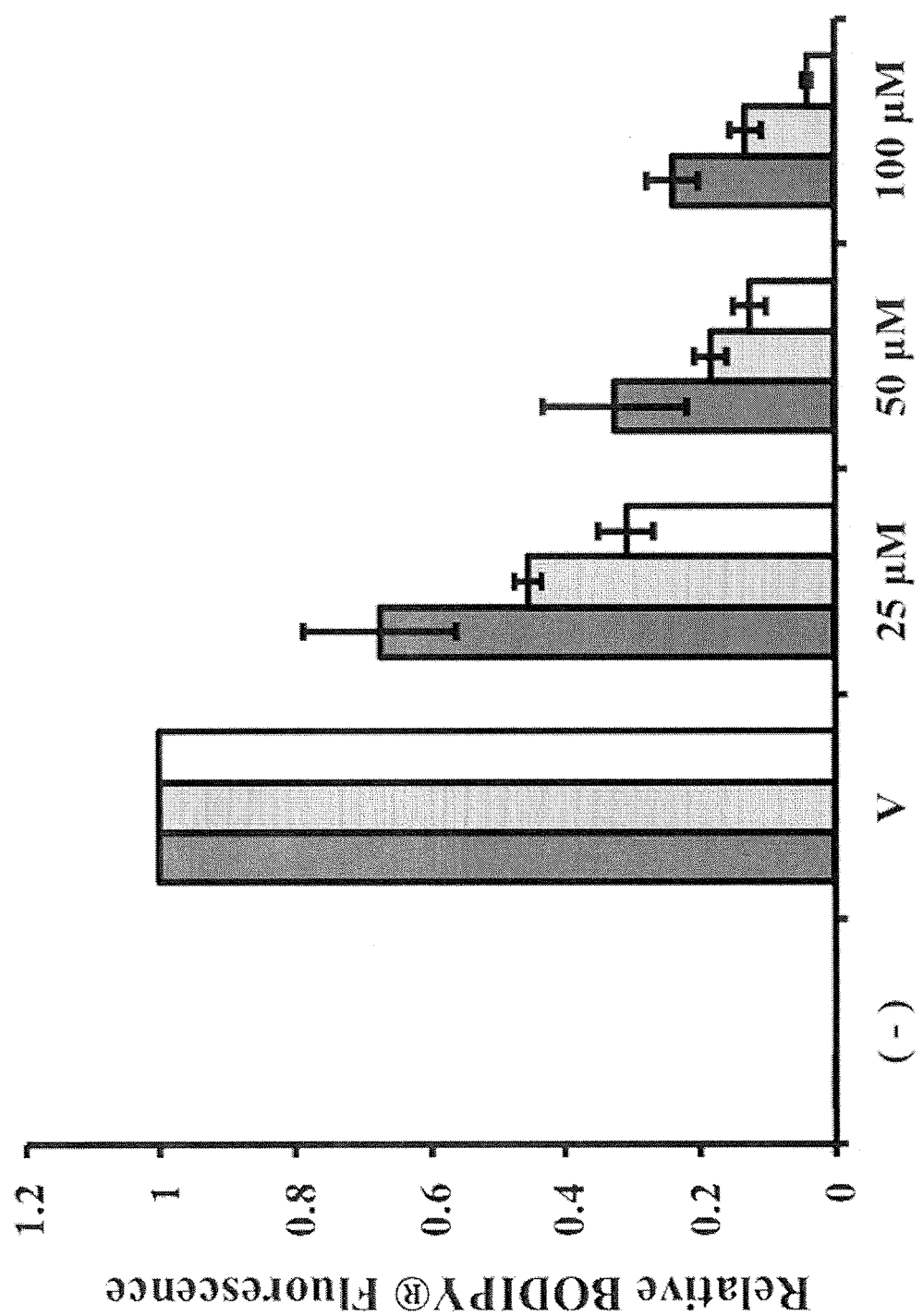
FIG. 8 shows inhibition of palmitoyl-CoA concentration dependent palmitoylation of Erf2 by Compound 13. Orthogonal screen of steady-state Erf2 auto-palmitoylation with compound 13 at 25 µM (dark grey bars), 50 µM (light grey bars) and 100 µM (white bars) was separated by SDS-PAGE. The average relative BODIPY® fluorescence from three reactions that comigrated with Erf2 is presented as a fraction of vehicle control (VC; 5% DMF) for each concentration of BODIPY®-C12-CoA +/−standard deviation. A reaction lacking Erf2 (−) represents baseline activity in the assay. Prior experiments in this study used 100 µM Compound 13 with 40 µM BODIPY®-012-CoA.

The mode of inhibition was also explored for effects on steady-state autopalmitoylation using the gel-based orthogonal assay. Compound 13 exhibits a greater dosage response for Erf2 autopalmitoylation inhibition at lower BODIPY®-C12-CoA concentrations rather than at higher BODIPY®-C12-CoA concentrations, supporting that compound 13 is acting competitively with BODIPY®-C12-CoA (FIG. 8). Conversely, 2-BP has been previously demonstrated as an uncompetitive or mixed inhibitor of Erf2 autopalmitoylation [13], demonstrating that compounds 13 and 25 utilize a different inhibitory mechanism compared to 2-BP. Thus, we have identified a new class of palmitoylation inhibitors that are structurally distinct and utilize a mode of action different from the currently used palmitoylation inhibitor, 2-BP.

TABLE 1

The effect of varying the concentration of Compounds 13 and 25, and 2-BP on the Km and Vmax for the Palmitoyl-CoA substrate.

| | $K_M$ (μM) | $V_{MAX}$ (μM) | $R^2$ |
|---|---|---|---|
| Compound 13 (μM) | | | |
| 0 | 3 +/− 1 | 210 +/− 11 | 0.9 |
| 25 | 11 +/− 3 | 243 +/− 20 | 0.87 |
| 50 | 38 +/− 6 | 354 +/− 26 | 0.97 |
| 100 | 145 +/− 30 | 631 +/− 94 | 0.98 |
| Compound 25 (μM) | | | |
| 0 | 3 +/− 1 | 296 +/− 17 | 0.88 |
| 25 | 11 +/− 3 | 307 +/− 30 | 0.83 |
| 50 | 23 +/− 6 | 344 +/− 34 | 0.91 |
| 100 | 79 +/− 15 | 542 +/− 60 | 0.98 |
| 2-BP (μM) | | | |
| 0 | 4 +/− 1 | 222 +/− 7 | 0.96 |
| 25 | 2 +/− 1 | 160 +/− 5 | 0.95 |
| 50 | 10 +/− 6 | 126 +/− 23 | 0.53 |
| 100 | 14 +/− 7 | 51 +/− 8 | 0.71 |

Figure 9:
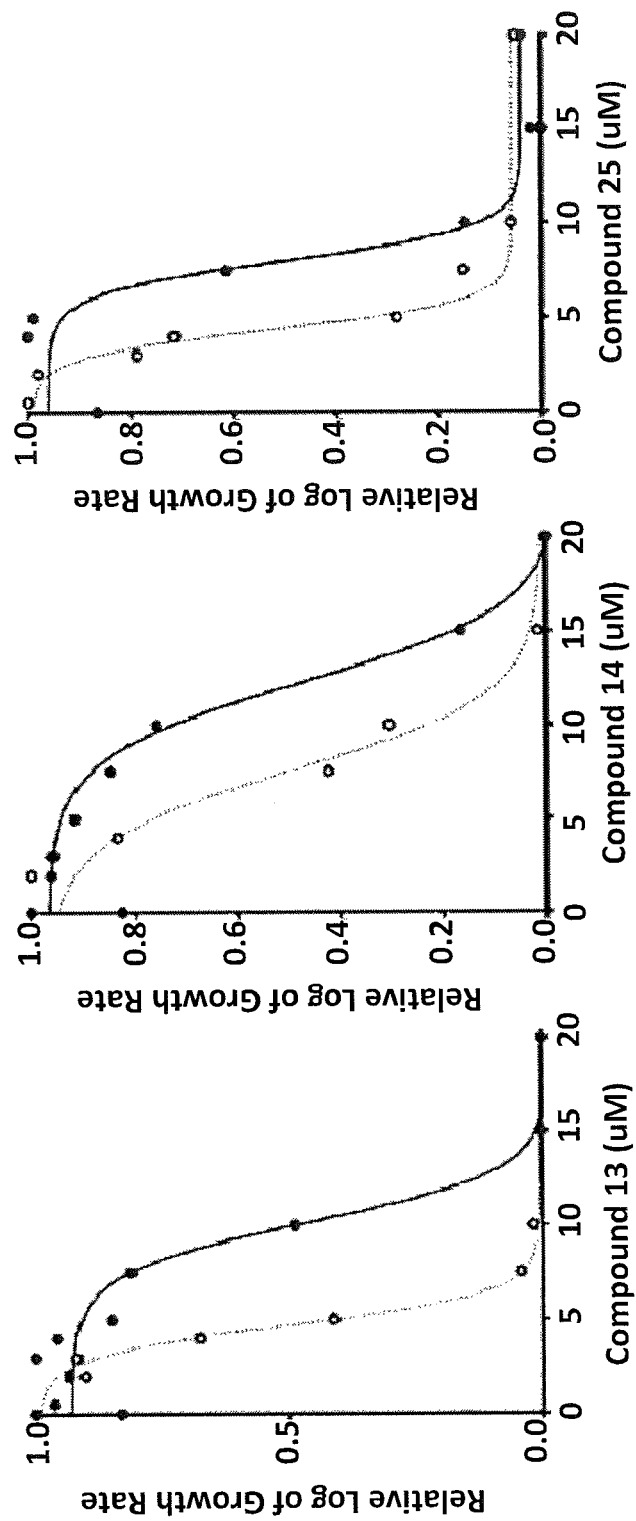
FIG. 9 shows the inhibition of Ras palmitoylation-sensitized yeast. The $EC_{50}$ for each of the individual compounds was established by graphing the logarithmic growth of *S. cerevisiae* strain, RJY1941 (solid lines and solid circles) and RJY1942 (hashed lines and open circles), versus the concentration of each compound. The curves were used to estimate the $EC_{50}$ values are presented for 2-BP and the ten compounds identified in this study. Values were normalized to visually compare relative log of the growth rate of each compound and 2-BP.
Figure 9:
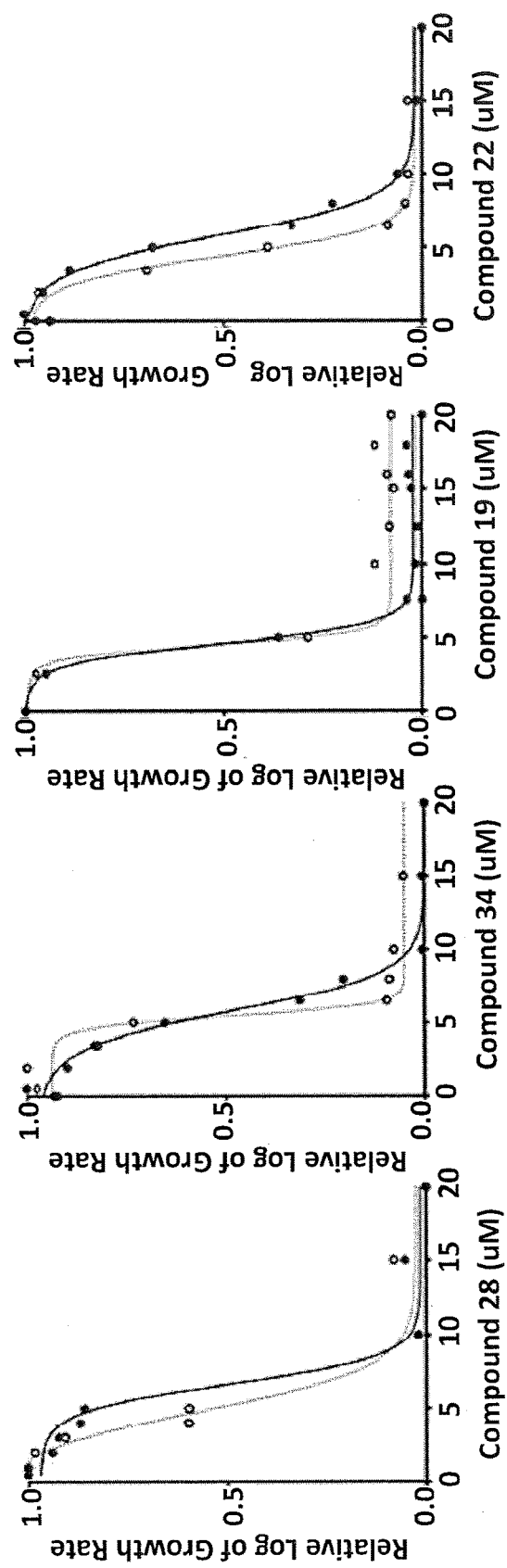
Figure 9:
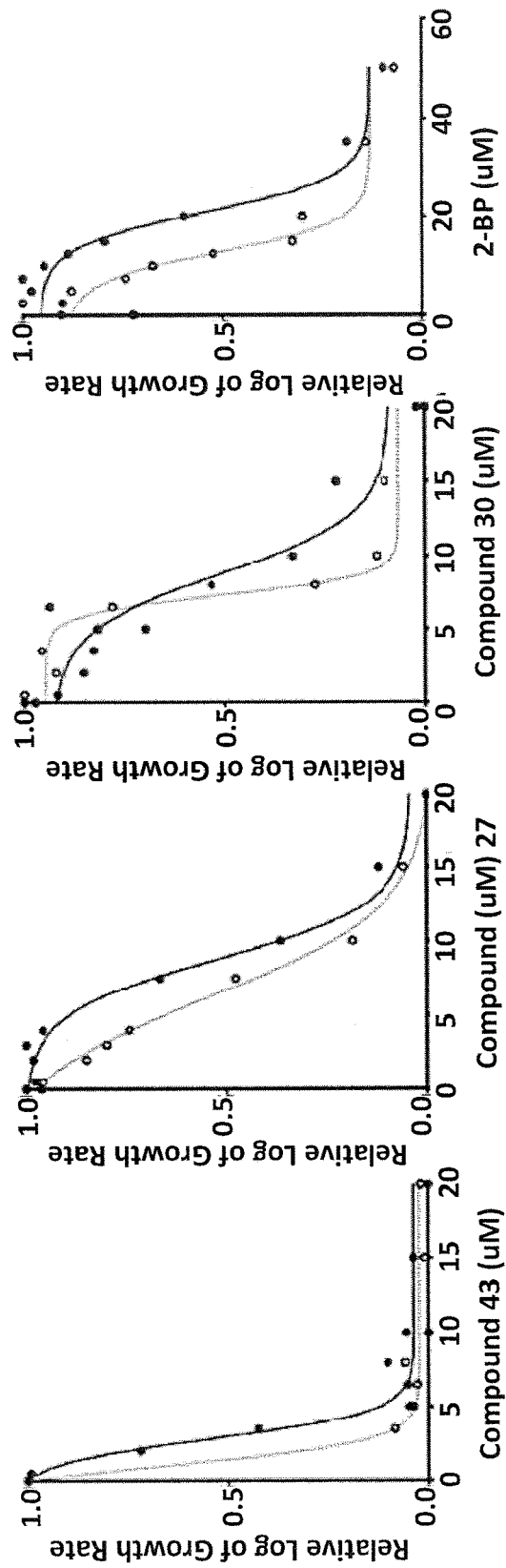

Inhibition of Ras-Dependent Growth in a Palmitoylation-Sensitive *S. cerevisiae* Strain To examine the inhibition of Ras palmitoylation in vivo, we utilized two strains of *S. cerevisiae*. The yeast strain RJY1942 (palmitoylation sensitive) requires Ras2 palmitoylation for viability [16]. The isogenic wild type control yeast strain (RJY1941) is not dependent on Ras2 palmitoylation for viability. The growth of both strains was monitored in the presence (or absence) of our inhibitors every 30 mins for 24 hrs. $EC_{50}$ values were calculated using GraphPad Prism® (La Jolla, Calif.) to extrapolate the effective concentration of each inhibitor that caused a 50% reduction in growth (FIG. 9). $EC_{50}$ values ranged from 2 μM to 7.5 μM in the sensitive strain, compared to 12.5 μM for 2-BP in the sensitive strain. Compounds 13, 25, and 2-BP show a modest selectivity for the sensitive strain, RJY1942, over the control strain, RJY1941, resulting in a 2-fold greater $EC_{50}$ value in the control strain as compared to the sensitive strain (values listed in FIG. 5, right panel). It is not clear at this time why only compounds 13 and 25 exhibit selectivity in the cell based assay, whereas there is the others inhibit the purified enzyme to a similar extent. Additional work is needed to determine the mechanism of growth inhibition and selectivity of these compounds.

Figure 10:
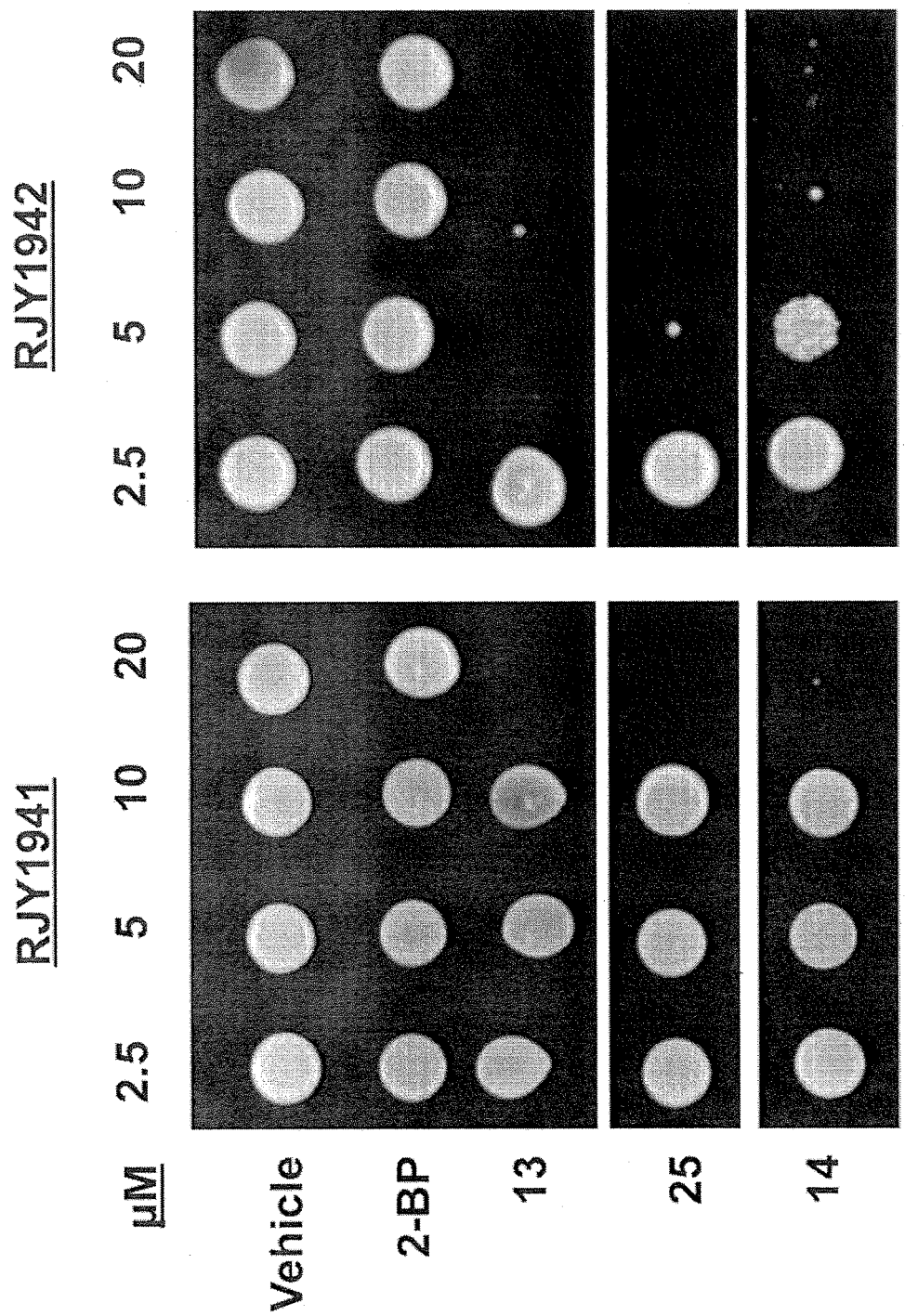
FIG. 10 demonstrates that compounds 13, 25, and 14 inhibit palmitoylated Ras-dependent growth in yeast. A representative (n=3) spot assay of cytotoxic effects in wild type (RJY1941) *S. cerevisiae* is compared to that of the palmitoylation-dependent (RJY1942) strain. Liquid cultures containing the shown inhibitors were spotted onto selective media and incubated at 30° C. for 3 days. The concentrations used in the liquid cultures for compounds 13, 25, 14 and 2-BP were 2.5 µM, 5 µM, 10 µM, and 20 µM in 1% DMF.

We next compared the ability of either strain to grow following the 24 hrs incubation with Compounds 13, 14, or 25. Serial dilutions of RJY1941 and RJY1942 were spotted on agar plates following incubation for 24 hrs with varying inhibitor concentrations. Compounds 13, 14, and 25 completely inhibited growth of RJY1941 (control) at 20 μM, but had no detectable effect at lower concentrations (FIG. 10). Conversely, compound 13 inhibited (100%) the growth of RJY1942 (sensitized) at 5 μM. Compound 25 also inhibited at 5 μM, albeit at approximately 90% of that observed for compound 13 for the sensitized strain. Compound 14 demonstrated partial inhibition (approximately 10%) at 5 μM, however, total inhibition could be observed for the sensitized strain at higher inhibitor concentrations. 2-BP did not inhibit, most likely due to poor permeability of 2-BP on solid yeast medium.

4. Discussion

Protein S-palmitoylation is a posttranslational modification that regulates the subcellular localization and activity of a diverse set of signaling and structural proteins. Dysregulation of protein palmitoylation has been linked to a number of diseases. Examples include up-regulation of zDHHC9 in colorectal cancer [27] and down-regulation of zDHHC9 in leukemogenesis [28]; zDHHC3/GODZ is linked to cervical cancer [29] and zDHHC2 mutations have been found in several colorectal cancers [30]. The importance of palmitoylation in physiology and pathophysiology suggests that modulators of catalyzed palmitoyl transfer may play a role in disease treatment. The availability of PAT inhibitors is very limited. 2-Bromo-palmitate (2-BP), cerulenin, and tunicamycin have been reported to inhibit palmitoylation [8, 31-33], but 2-BP is now known to be highly promiscuous, with no preference for CoA-dependent enzymes, including zDHHC PATs [9]. Similarly, cerulenin and tunicamycin inhibit palmitoylation within cells but also inhibit other cellular process including fatty acid synthesis [34] and N-glycosylation [35], respectively. In addition, there are few assays available that can measure palmitoylation [3, 13] in a high throughput platform. There is therefore a need to establish methods to identify small molecule PAT inhibitors for use in vitro and in vivo.

The current lack of high affinity, specific inhibitors is due in part to difficulties purifying biochemical quantities of PATs, limited information on the enzymatic mechanism and the lack of a 3D crystal structure. We have developed methods to purify stable, active zDHHC PATs, along with a validated HTS method to identify inhibitors. This has allowed the search for chemical modulators of PAT enzymes using HTS coupled with counter screens, orthogonal validation and cell-based assays, to characterize and analyze candidate inhibitors. With these tools in hand we are able to identify compounds that regulate the Ras PAT, Erf2.

Through the use of a scaffold ranking approach to screen for novel inhibitors of Erf2 autopalmitoylation, we have identified a group of inhibitors based on the bis-cyclic piperazine backbone. Piperazine analogues have already been demonstrated to be effective drug-like compounds. They are currently used as pharmaceutical modulators of GPCR activity and piperazine-like compounds and analogs are also used as pharmaceuticals to treat cancer, behavioral disorders, and insomnia (e.g., imatinib, quetiapine, and eszopiclone) [36-38]. To further explore their specificity for use as modulators of palmitoylation, there is ongoing work to address any inhibitor:enzyme specificity issues by establishing if the inhibitors identified in this study act specifically on Erf2-dependent palmitoylation, or if they act on one or more of the other PAT enzymes. Further analysis will be needed to validate these compounds as pan inhibitors of palmitoylation, which would be beneficial over 2-BP due to the extent of non-specific inhibition that occurs with the use of 2-BP. Specific inhibitors of Erf2 and its human homolog, zDHHC9, will be beneficial for anti-cancer drug therapy interventions. Understanding how the different functional groups lend to their activity and specificity is key to further optimize these compounds. The compounds best align with the $K_i$ and $EC_{50}$ values from the respective screens when they were organized by the R3 position with consideration of the R1 and R2 positions (FIG. 5). Of the functionalities used at the R1 and R3 positions both 2-(4-Isobutyl-phenyl)-propyl and 2-(3,5-bis-trifluoromethyl-phenyl)-ethyl were the most preferential for both positions. This, along with the apparent symmetry of bis-piperazine, suggests that perhaps these compounds can act as symmetrical entities. The lack of preference, other than for an aromatic group, in the R2 position supports this notion.

Conclusion

We have identified a novel class of bis-cyclic piperazines that inhibit Erf2 autopalmitoylation utilizing a fluorescence-based coupled assay, orthogonal gel-based assay and cell growth assay. A subset of these bis-cyclic piperazines shows Ras-dependent inhibition of yeast cells in vivo.

Supplemental Materials and Methods

Figure 11:
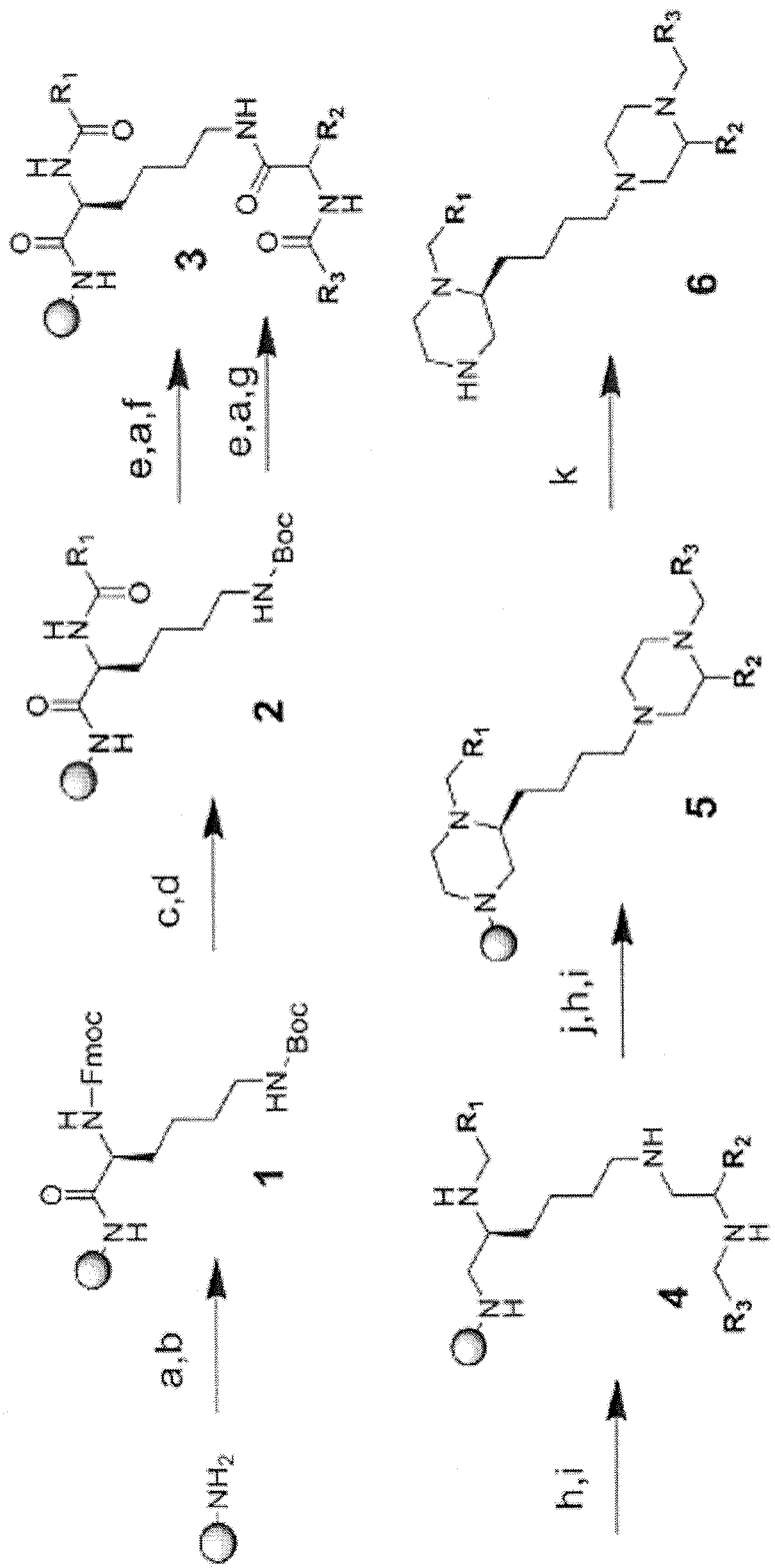
FIG. 11 illustrates the general synthesis of bis-cyclic piperazine.

Supplemental 1. Synthesis of Library 2160 and Individual Compounds and Construction of Scaffold Ranking Plate General Synthesis of bis-cyclic piperazine (FIG. 11): Library 2160 as well as the individual compounds reported herein (Compounds 1-54) were synthesized following the same synthetic scheme (FIG. 11) (14,15). Utilizing the "tea-bag" methodology (16), 100 mg of p-methylbenzhydrylamine (MBHA) resin (1.1 mmol/g, 100-200 mesh) was sealed in a mesh "teabag", neutralized with 5% diisopropylethylamine (DIEA) in dichloromethane (DCM) and subsequently swelled with additional DCM washes. Fmoc-L-Lys (Boc)-OH was coupled in Dimethylformamide (0.1M DMF) for 120 mins in the presence of Diisopropylcarbodiimide (DIC, 6 equiv.) and 1-Hydroxybenzotriazole hydrate (HOBt, 6 equiv.) (Step 1, FIG. 11). The Fmoc protecting group was removed with 20% piperidine in DMF for 20 mins and the R1 carboxylic acids was coupled (10 equiv.) in the presence of DIC (10 equiv.) and HOBt (10 equiv.) in DMF (0.1 M) for 120 mins (Step 2, FIG. 11). The Boc protecting group was then removed with Trifluoroacetic Acid (TFA) in DCM for 30 mins and subsequently neutralized with 5% DIEA/DCM (3x). Boc-Amino Acids (R2) were coupled utilizing standard coupling procedures (6 equiv.) with DIC (6 equiv.) and HOBt (6 equiv.) in DMF (0.1 M) for 120 mins. The Boc group was removed with 55% TFA/DCM for 30 mins and subsequently neutralized with 5% DIEA/DCM (3x). Carboxylic acids (R3) were coupled using (10 equiv.) in the presence of DIC (10 equiv.) and HOBt (10 equiv.) in DMF (0.1 M) for 120 mins (Step 3, FIG. 11). All coupling reactions were monitored for completion using Ninhydrin. The reduction was performed in a 4000 mL Wilmad Lab-Glass vessel under nitrogen. 1.0 M Tetrahydrofuran (THF) borane complex solution was used in 40-fold excess for each amide bond. The vessel was heated to 65° C. and maintained at this temperature for 96 hrs. The solution was then removed and the bags were washed with THF and methanol (MeOH). Once completely dry, the bags were treated overnight with piperidine at 65° C. and washed several times with DMF, DCM and methanol (Step 4, FIG. 11). As previously reported by our group and others, the reduction of polyamides with borane is free of racemization (17-19). Before proceeding, completion of reduction was monitored by LCMS analysis of a control compound (Step 4, FIG. 11) that was cleaved from the solid support (HF, anisole, 0° C. 7 hr). Cyclization was performed with a 5-fold excess (for each cyclization) of oxalyldiimidazole in a 0.1 M anhydrous DMF solution overnight. Following the cyclization, the bags were rinsed with DMF and DCM and the resulting diketopiperarzines were reduced down to their corresponding piperazines (Step 5, FIG. 11) using the same borane reduction procedure as above. The resin was cleaved with HF in the presence of anisole in an ice bath at 0° C. for 7 hours (Step 6, FIG. 11). After removal of the HF by gaseous $N_2$, the products were then extracted from the vessels with 95% acetic acid in water, transferred to scintillation vials, frozen and lyophilized. The compounds were then reconstituted in 50% acetonitrile and water, frozen and lyophilized three more times. For initial screening (FIG. 4) the individual compounds were tested as crude material in case the activity is driven by some side reaction that was also present in the original positional scanning library. After this initial screening, compounds, 13, 14, 19, 22, 25, 27, 28, 30, 34, and 43 were selected for purification and NMR characterization; all data reported in FIGS. 6-9 are from the purified stock of these compounds.

Supplemental 2. LCMS Analysis

The purity and identity of all compounds was verified using a Shimadzu 2010 LCMS system, consisting of a LC-20AD binary solvent pump, a DGU-20A degasser unit, a CTO-20A column oven, and a SIL-20A HT autosampler. A Shimadzu SPD-M20A diode array detector was used for detection. A full spectra range of 190-600 nm was obtained during analysis. Chromatographic separations were obtained using a Phenomenex Luna C18 analytical column (5 μm, 50×4.6 mm i.d.) preceded by a Phenomenex C18 column guard (5 μm, 4×3.0 mm i.d.). All equipment was controlled and integrated by Shimadzu LCMS solutions software version 3. Mobile phases for LCMS analysis were HPLC grade or LCMS grade obtained from Sigma Aldrich and Fisher Scientific. The mobile phases consisted of a mixture LCMS grade Acetonitrile/water (both with 0.1% formic acid for a pH of 2.7). The initial setting for analysis was set at 5% Acetonitrile (v/v), then was linearly increased to 95% Acetonitrile over 6 mins. The gradient was then held at 95% Acetonitrile for 2 mins, linearly decreased to 5% over 0.10 mins and held for an additional 1.90 mins. The total run time was equal to 12 mins. The total flow rate was set to 0.5 mL/minute. The column oven and flow cell temperature for the diode array detector was set at 30° C. The autosampler temperature was held at 15° C. 5 μl of compound was injected for analysis.

Supplemental 3. HPLC Purification (Compounds 13, 14, 19, 22, 25, 27, 28, 30, 34, and 43)

All purifications were performed on a Shimadzu Prominence preparative HPLC system, consisting of LC-8A binary solvent pump, a SCL-10A system controller, a SIL-10AP autosampler, and a FRC-10A fraction collector. A Shimadzu SPD-20A UV detector was used for detection. The wavelength was set at 214 nm during analysis. Chromatographic separations were obtained using a Phenomenex Luna C18 preparative column (5 μm, 150×21.5 mm i.d.) preceded by a Phenomenex C18 column guard (5 μm, 15×21.2 mm i.d.). Prominence prep software was used to set all detection and collection parameters. The mobile phases for HPLC purification were HPLC grade obtained from Sigma Aldrich and Fisher Scientific. The mobile phase consisted of a mixture of Acetonitrile/water (both with 0.1% formic acid). The initial setting for separation was set at 2% (v/v) Acetonitrile, which was held for 2 mins and the gradient was linearly increased to 20% (v/v) Acetonitrile over 4 mins. The gradient was then linearly increased to 55% (v/v) Acetonitrile over 36 mins. The HPLC system was set to automatically flush and re-equilibrate the column after each run for a total of 4 column volumes. The total flow rate was set to 12 mL/min and the total injection volume was set to 3900 μl. The fraction collector was set to collect from 6 to 40 mins. The corresponding fractions were then combined and lyophilized.

Supplemental 4. NMR Analysis of Purified Compounds

The 1H spectra were obtained utilizing the Bruker 400 Ascend (400 MHz). NMR chemical shifts were reported in δ (ppm) using the δ 7.26 signal of CDCl3 (1H NMR).

Supplemental 5. Chemical Synthesis of Individual Compounds 4-(((2S)-1-(2-(4-isobutylphenyl)propyl)-4-(4-((2S)-1-(2-(4-isobutylphenyl)propyl)piperazin-2-yl)butyl) piperazin-2-yl)methyl)phenol (Compound 13)

Using the synthetic approach described in FIG. 1 for the synthesis of compound 13 was synthesized using the following reagents: 4-Isobutyl-alpha-methylphenylacetic acid (R1), Boc-L-Tyrosine(BrZ) (R2), 4-Isobutyl-alpha-methylphenylacetic acid (R3). Final crude product was purified by HPLC as described above. 1H NMR (400 MHz, CHLOROFORM-d): δ ppm 7.28 (br. s., 1H) 7.08-7.16 (m, 4H) 7.05 (br. s., 4H) 6.92 (br. s., 2H) 6.80 (br. s., 3H) 2.98 (br. s., 8H) 2.64-2.84 (m, 5H) 2.58 (br. s., 4H) 2.45 (t, J=8.01 Hz, 6H) 2.32 (d, J=16.26 Hz, 2H) 2.01 (br. s., 1H) 1.86 (d, J=6.60 Hz, 2H) 1.52 (br. s., 1H) 1.42 (br. s., 1H) 1.36 (br. s., 1H) 1.30 (br. s., 3H) 1.12-1.26 (m, 4H) 1.01 (br. s., 1H) 0.91 (br. s., 12H). LCMS (ESI+) Calcd for C45H68N4O: 681.54, found [M+H]+:681.25.

4-(((2S)-1-(3,5-bis(trifluoromethyl)phenethyl)-4-(4-((2S)-1-(2-(4-isobutylphenyl)propyl)piperazin-2-yl) butyl)piperazin-2-yl)methyl)phenol (Compound 14)

Using the synthetic approach described in FIG. 1 for the synthesis of compound 14 was synthesized using the following reagents: 4-Isobutyl-alpha-methylphenylacetic acid (R1), Boc-L-Tyrosine(BrZ) (R2), 3,5-Bis(Trifluoromethyl)-Phenylacetic Acid (R3). Final crude product was purified by HPLC as described above. 1H NMR (400 MHz, CHLOROFORM-d): δ ppm 7.75 (br. s., 1H) 7.65 (br. s., 3H) 7.28 (s, 1H) 7.00-7.08 (m, 4H) 6.95 (br. s., 2H) 6.81 (br. s., 3H) 3.07 (br. s., 5H) 2.93 (br. s., 5H) 2.76 (br. s., 4H) 2.65 (br. s., 4H) 2.43 (d, J=6.36 Hz, 4H) 2.36 (br. s., 2H) 2.19 (br. s., 1H) 2.01 (br. s., 1H) 1.84 (br. s., 1H) 1.47 (br. s., 2H) 1.39 (br. s., 1H) 1.27 (br. s., 1H) 1.22 (br. s., 3H) 1.05 (br. s., 1H) 0.90 (d, J=5.50 Hz, 6H). LCMS (ESI+) Calcd for C42H56F6N4O: 747.44, found [M+H]+:747.20.

(2S)-1-(2-(4-isobutylphenyl)propyl)-4-(4-((2S)-1-(2-(4-isobutylphenyl)propyl)piperazin-2-yl)butyl)-2-(naphthalen-2-ylmethyl)piperazine (Compound 19)

Using the synthetic approach described in FIG. 1 for the synthesis of compound 19 was synthesized using the following reagents: 4-Isobutyl-alpha-methylphenylacetic acid (R1), Boc-3-(2-naphthyl)-L-alanine (R2), 4-Isobutyl-alpha-methylphenylacetic acid (R3). Final crude product was purified by HPLC as described above. 1H NMR (400 MHz, CHLOROFORM-d): δ ppm 7.78 (d, J=9.05 Hz, 3H) 7.61 (br. s., 1H) 7.44 (br. s., 2H) 7.29 (br. s., 1H) 6.99-7.20 (m, 7H) 4.16 (br. s., 1H) 3.09-3.34 (m, 1H) 3.00 (d, J=12.59 Hz, 3H) 2.91 (br. s., 2H) 2.84 (br. s., 2H) 2.78 (br.s., 2H) 2.58 (d, J=12.84 Hz, 2H) 2.45 (dd, J=15.89, 6.72 Hz, 7H) 2.28 (br. s., 3H) 2.20 (br. s., 2H) 1.97 (br. s., 1H) 1.86 (dd, J=13.08, 6.85 Hz, 2H) 1.60 (br. s., 1H) 1.18-1.46 (m, 9H) 1.15 (br. s., 2H) 0.70-0.95 (m, 12H). LCMS (ESI+) Calcd for C49H70N4: 715.56, found [M+H]+:715.30.

(2R)-1-(2-(4-isobutylphenyl)propyl)-4-(4-((2S)-1-(2-(4-isobutylphenyl)propyl)piperazin-2-yl)butyl)-2-(naphthalen-2-ylmethyl)piperazine (Compound 22)

Using the synthetic approach described in FIG. 1 for the synthesis of compound 22 was synthesized using the following reagents: 4-Isobutyl-alpha-methylphenylacetic acid (R1), Boc-L-Tyrosine(BrZ) (R2), 4-Isobutyl-alpha-methylphenylacetic acid (R3). Final crude product was purified by HPLC as described above. 1H NMR (400 MHz, CHLOROFORM-d): δ ppm 7.71-7.85 (m, 3H) 7.60 (br. s., 1H) 7.44 (br. s., 2H) 7.28-7.35 (m, 1H) 7.01-7.26 (m, 8H) 3.19 (d, J=10.15 Hz, 1H) 2.94-3.07 (m, 3H) 2.89 (d, J=9.66 Hz, 3H) 2.82 (br. s., 3H) 2.60-2.74 (m, 2H) 2.55 (br. s., 1H) 2.24-2.50 (m, 10H) 2.19 (br. s., 2H) 1.97 (br. s., 1H) 1.74-1.92 (m, 2H)

4-(((2S)-4-(4-((S)-1-(3,5-bis(trifluoromethyl)phenethyl)piperazin-2-yl)butyl)-1-(2-(4-isobutylphenyl)propyl)piperazin-2-yl)methyl)phenol (Compound 25)

Using the synthetic approach described in FIG. 1 for the synthesis of compound 25 was synthesized using the following reagents: 3,5-Bis(Trifluoromethyl)-Phenylacetic Acid (R1), Boc-L-Tyrosine(BrZ) (R2), 4-Isobutyl-alpha-methylphenylacetic acid (R3). Final crude product was purified by HPLC as described above. 1H NMR (400 MHz, CHLOROFORM-d): δ ppm 7.74 (br. s., 2H) 7.62 (br. s., 1H) 7.29 (s, 2H) 7.07-7.26 (m, 4H) 6.93 (s, 1H) 6.96 (s, 1H) 6.82 (d, J=6.97 Hz, 2H) 3.19 (br. s., 2H) 3.10 (br. s., 2H) 3.00 (br. s., 5H) 2.84 (br. s., 5H) 2.70 (br. s., 4H) 2.62 (br. s., 3H) 2.46 (d, J=6.60 Hz, 3H) 2.19 (br. s., 1H) 2.02 (br. s., 1H) 1.86 (br. s., 1H) 1.56 (br. s., 1H) 1.43 (br. s., 2H) 1.30 (br. s., 3H) 1.17 (d, J=6.24 Hz, 1H) 1.10 (br. s., 2H) 0.91 (d, J=6.11 Hz, 6H). LCMS (ESI+) Calcd for C42H56F6N4O: 747.44, found [M+H]+:747.10.

4-(((S)-1-(adamantan-1-ylmethyl)-4-(4-((S)-1-(3,5-bis(trifluoromethyl)phenethyl)piperazin-2-yl)butyl)piperazin-2-yl)methyl)phenol (Compound 27)

Using the synthetic approach described in FIG. 1 for the synthesis of compound 27 was synthesized using the following reagents: 3,5-Bis(Trifluoromethyl)-Phenylacetic Acid (R1), Boc-L-Tyrosine(BrZ) (R2), 1-Adamantanecarboxylic Acid (R3). Final crude product was purified by HPLC as described above. 1H NMR (400 MHz, CHLOROFORM-d): δ ppm 8.44 (br. s., 1H) 8.05 (br. s., 1H) 7.96 (br. s., 1H) 7.83 (br. s., 1H) 7.73 (br. s., 1H) 7.63 (br. s., 2H) 7.28 (s, 1H) 7.00 (br. s., 2H) 6.83 (d, J=6.48 Hz, 2H) 3.17 (br. s., 1H) 2.91-3.13 (m, 5H) 2.84 (br. s., 5H) 2.54-2.77 (m, 7H) 2.40 (br. s., 2H) 2.10 (br. s., 1H) 1.99 (d, J=6.36 Hz, 4H) 1.69-1.85 (m, 3H) 1.64 (d, J=11.37 Hz, 4H) 1.50 (br. s., 8H) 1.28 (br. s., 1H) 1.13 (br. s., 2H). LCMS (ESI+) Calcd for C40H54F6N4O: 721.42, found [M+H]+:721.15.

(2S)-4-(4-((S)-1-(3,5-bis(trifluoromethyl)phenethyl)piperazin-2-yl)butyl)-1-(2-(4-isobutylphenyl)propyl)-2-phenylpiperazine (Compound 28)

Using the synthetic approach described in FIG. 1 for the synthesis of compound 28 was synthesized using the following reagents: 3,5-Bis(Trifluoromethyl)-Phenylacetic Acid (R1), Boc-L-Phenylglycine (R2), 4-Isobutyl-alpha-methylphenylacetic acid (R3). Final crude product was purified by HPLC as described above. 1H NMR (400 MHz, CHLOROFORM-d): δ ppm 7.74 (br. s., 1H) 7.65 (br. s., 2H) 7.28-7.40 (m, 2H) 7.12-7.26 (m, 2H) 6.85-7.07 (m, 5H) 3.43-3.66 (m, 1H) 3.36 (br. s., 1H) 3.30 (d, J=7.58 Hz, 1H) 3.22 (d, J=11.37 Hz, 1H) 3.15 (br. s., 1H) 3.02 (br. s., 2H) 2.83-2.96 (m, 6H) 2.78 (d, J=11.37 Hz, 1H) 2.53-2.72 (m, 2H) 2.36-2.52 (m, 4H) 2.26-2.36 (m, 3H) 2.21 (br. s., 1H) 1.98-2.16 (m, 2H) 1.76-1.96 (m, 2H) 1.48 (br. s., 3H) 1.36 (br. s., 1H) 1.27 (br. s., 1H) 1.20 (d, J=6.24 Hz, 2H) 1.08 (d, J=6.24 Hz, 2H) 0.96 (d, J=5.99 Hz, 3H) 0.88 (d, J=6.11 Hz, 3H). LCMS (ESI+) Calcd for C41H54F6N4: 717.43, found [M+1-1]+:17.15.

(S)-1-(adamantan-1-ylmethyl)-4-(4-((S)-1-(3,5-bis(trifluoromethyl)phenethyl)piperazin-2-yl)butyl)-2-phenylpiperazine (Compound 30)

Using the synthetic approach described in FIG. 1 for the synthesis of compound 30 was synthesized using the following reagents: 3,5-Bis(Trifluoromethyl)-Phenylacetic Acid (R1), Boc-L-Phenylglycine (R2), 1-Adamantanecarboxylic Acid (R3). Final crude product was purified by HPLC as described above. 1H NMR (400 MHz, CHLOROFORM-d): δ ppm 7.74 (br. s., 1H) 7.66 (br. s., 2H) 7.35 (br. s., 2H) 7.28-7.32 (m, 2H) 3.49-3.76 (m, 3H) 3.34-3.49 (m, 1H) 3.15-3.33 (m, 2H) 3.03 (d, J=10.64 Hz, 2H) 2.78-2.96 (m, 6H) 2.59-2.73 (m, 2H) 2.48-2.58 (m, 1H) 2.45 (br. s., 1H) 2.28-2.43 (m, 4H) 2.20 (t, J=9.90 Hz, 1H) 2.10 (d, J=13.57 Hz, 1H) 2.01 (br. s., 1H) 1.87 (br. s., 3H) 1.71 (br. s., 1H) 1.64 (d, J=11.98 Hz, 3H) 1.55 (d, J=12.10 Hz, 4H) 1.35-1.51 (m, 6H) 1.25 (s, 3H) 1.23 (s, 2H). LCMS (ESI+) Calcd for C39H52F6N4: 691.41, found [M+1-1]+:691.10.

(2R)-4-(4-((S)-1-(3,5-bis(trifluoromethyl)phenethyl)piperazin-2-yl)butyl)-1-(2-(4-isobutylphenyl)propyl)-2-(naphthalen-2-ylmethyl)piperazine (Compound 34)

Using the synthetic approach described in FIG. 1 for the synthesis of compound 34 was synthesized using the following reagents: 3,5-Bis(Trifluoromethyl)-Phenylacetic Acid (R1), Boc-3-(2-naphthyl)-D-alanine (R2), 4-Isobutyl-alpha-methylphenylacetic acid (R3). Final crude product was purified by HPLC as described above. 1H NMR (400 MHz, CHLOROFORM-d): δ ppm 7.71-7.82 (m, 4H) 7.59 (s, 1H) 7.63 (s, 2H) 7.43 (br. s., 2H) 7.28 (br. s., 1H) 7.07-7.20 (m, 4H) 3.54 (br. s., 2H) 3.33 (br. s., 1H) 3.19 (d, J=10.64 Hz, 2H) 3.01 (br. s., 3H) 2.89 (br. s., 4H) 2.83 (br. s., 4H) 2.61 (br. s., 2H) 2.56 (br. s., 2H) 2.40-2.52 (m, 5H) 2.36 (br. s., 1H) 2.26 (br. s., 1H) 2.19 (br. s., 2H) 1.88 (d, J=5.99 Hz, 1H) 1.39 (br. s., 3H) 1.27-1.37 (m, 4H) 1.23 (br. s., 1H) 1.16 (br. s., 1H) 0.92 (br. s., 6H). LCMS (ESI+) Calcd for C46H58F6N4: 781.46, found [M+H]+:781.15.

(2S)-4-(4-((S)-1-((4-(tert-butyl)cyclohexyl)methyl)piperazin-2-yl)butyl)-1-(2-(4-isobutylphenyl)propyl)-2-(naphthalen-2-ylmethyl)piperazine (Compound 43)

Using the synthetic approach described in FIG. 1 for the synthesis of compound 43 was synthesized using the following reagents: 4-tert-Butyl-Cyclohexanecarboxylic Acid (R1), Boc-3-(2-naphthyl)-L-alanine (R2), 4-Isobutyl-alpha-methylphenylacetic acid (R3). Final crude product was purified by HPLC as described above. 1H NMR (400 MHz, CHLOROFORM-d): δ ppm 7.71-7.84 (m, 3H) 7.60 (br. s., 1H) 7.45 (br. s., 2H) 7.29 (br. s., 1H) 7.02-7.26 (m, 4H) 3.18 (d, J=9.54 Hz, 1H) 3.04 (br. s., 2H) 2.97 (br. s., 2H) 2.91 (br. s., 3H) 2.83 (br. s., 1H) 2.73 (d, J=9.54 Hz, 2H) 2.52-2.67 (m, 2H) 2.48 (br. s., 3H) 2.41 (br. s., 2H) 2.31 (br. s., 2H) 2.22 (br. s., 2H) 1.91-2.09 (m, 2H) 1.88 (d, J=7.34 Hz, 1H) 1.75 (d, J=13.94 Hz, 2H) 1.60 (d, J=13.20 Hz, 1H) 1.50 (br. s., 3H) 1.43 (br. s., 3H) 1.26-1.38 (m, 5H) 1.21 (br. s., 2H) 0.89-1.06 (m, 9H) 0.65-0.89 (m, 10H). LCMS (ESI+) Calcd for C47H72N4: 694.58, found [M+H]+:694.40.

REFERENCES

[1] Chamberlain, L. H. Shipston, M. J. The physiology of protein S-acylation. *Physiological reviews*, 2015, 95, 341-76.

[2] Rocks, O.; Peyker, A.; Kahms, M.; Verveer, P. J.; Koerner, C.; Lumbierres, M.; Kuhlmann, J.; Waldmann, H.; Wittinghofer, A. Bastiaens, P. I. An acylation cycle regulates localization and activity of palmitoylated Ras isoforms. *Science,* 2005, 307, 1746-52.

[3] Mitchell, D. A.; Mitchell, G.; Ling, Y.; Budde, C. Deschenes, R. J. Mutational analysis of *Saccharomyces cerevisiae* Erf2 reveals a two-step reaction mechanism for protein palmitoylation by DHHC enzymes. *J Biol Chem,* 2010, 285, 38104-14.

[4] Jennings, B. C. Linder, M. E. DHHC protein S-acyltransferases use similar ping-pong kinetic mechanisms but display different acyl-CoA specificities. *J Biol Chem,* 2012, 287, 7236-45.

[5] Ohno, Y.; Kihara, A.; Sano, T. Igarashi, Y. Intracellular localization and tissue-specific distribution of human and yeast DHHC cysteine-rich domain-containing proteins. *Biochimica et biophysica acta,* 2006, 1761, 474-83.

[6] Roth, A. F.; Wan, J.; Bailey, A. O.; Sun, B.; Kuchar, J. A.; Green, W. N.; Phinney, B. S.; Yates, J. R., 3rd Davis, N. G. Global analysis of protein palmitoylation in yeast. *Cell,* 2006, 125, 1003-13.

[7] Yeste-Velasco, M.; Linder, M. E. Lu, Y. J. Protein S-palmitoylation and cancer. *Biochimica et biophysica acta,* 2015, 1856, 107-120.

[8] Webb, Y.; Hermida-Matsumoto, L. Resh, M. D. Inhibition of protein palmitoylation, raft localization, and T cell signaling by 2-bromopalmitate and polyunsaturated fatty acids. *J Biol Chem,* 2000, 275, 261-70.

[9] Davda, D.; El Azzouny, M. A.; Tom, C. T.; Hernandez, J. L.; Majmudar, J. D.; Kennedy, R. T. Martin, B. R. Profiling targets of the irreversible palmitoylation inhibitor 2-bromopalmitate. *ACS chemical biology,* 2013, 8, 1912-7.

[10] Pedro, M. P.; Vilcaes, A. A.; Tomatis, V. M.; Oliveira, R. G.; Gomez, G. A. Daniotti, J. L. 2-Bromopalmitate reduces protein deacylation by inhibition of acyl-protein thioesterase enzymatic activities. *PloS one,* 2013, 8, e75232.

[11] Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D. Schneider, J. Strategies for the use of mixture-based synthetic combinatorial libraries: scaffold ranking, direct testing in vivo, and enhanced deconvolution by computational methods. *J Comb Chem,* 2008, 10, 3-19.

[12] Santos, R. G.; Appel, J. R.; Giulianotti, M. A.; Edwards, B. S.; Sklar, L. A.; Houghten, R. A. Pinilla, C. The mathematics of a successful deconvolution: a quantitative assessment of mixture-based combinatorial libraries screened against two formylpeptide receptors. *Molecules,* 2013, 18, 6408-24.

[13] Hamel, L. D.; Deschenes, R. J. Mitchell, D. A. A Fluorescence-Based Assay to Monitor Autopalmitoylation of zDHHC Proteins Applicable to High Throughput Screening. *Analytical biochemistry,* 2014,

[14] Sherman, F.; Fink, G. R. Hicks, J. B. *Laboratory course manual: Methods in yeast genetics,* Cold Spring Harbor Laboratory: Cold Spring Harbor, N.Y., 1986.

[15] Ito, H.; Fukada, Y.; Murata, K. Kimura, A. Transformation of intact yeast cells treated with alkali cations. *J. Bacteriol.,* 1983, 153, 163-168.

[16] Bartels, D. J.; Mitchell, D. A.; Dong, X. Deschenes, R. J. Erf2, a novel gene product that affects the localization and palmitoylation of Ras2 in *Saccharomyces cerevisiae. Mol Cell Biol,* 1999, 19, 6775-87.

[17] Ostresh, J. M.; Wnkle, J. H.; Hamashin, V. T. Houghten, R. A. Peptide libraries: determination of relative reaction rates of protected amino acids in competitive couplings. *Biopolymers,* 1994, 34, 1681-9.

[18] Houghten, R. A.; Pinilla, C.; Appel, J. R.; Blondelle, S. E.; Dooley, C. T.; Eichler, J.; Nefzi, A. Ostresh, J. M. Mixture-based synthetic combinatorial libraries. *J Med Chem,* 1999, 42, 3743-78.

[19] Pinilla, C.; Appel, J. R.; Blanc, P. Houghten, R. A. Rapid identification of high affinity peptide ligands using positional scanning synthetic peptide combinatorial libraries. *Biotechniques,* 1992, 13, 901-5.

[20] Acharya, A. N.; Ostresh, J. M. Houghten, R. A. Determination of isokinetic ratios necessary for equimolar incorporation of carboxylic acids in the solid-phase synthesis of mixture-based combinatorial libraries. *Biopolymers,* 2002, 65, 32-9.

[21] Santos, R. G.; Giulianotti, M. A.; Dooley, C. T.; Pinilla, C.; Appel, J. R. Houghten, R. A. Use and implications of the harmonic mean model on mixtures for basic research and drug discovery. *ACS combinatorial science,* 2011, 13, 337-44.

[22] Santos, R. G.; Giulianotti, M. A., Houghten, R. A. Medina-Franco, J. L. Conditional probabilistic analysis for prediction of the activity landscape and relative compound activities. *J Chem Inf Model,* 2013, 53, 2613-25.

[23] Minond, D.; Cudic, M.; Bionda, N.; Giulianotti, M.; Maida, L.; Houghten, R. A. Fields, G. B. Discovery of novel inhibitors of a disintegrin and metalloprotease 17 (ADAM17) using glycosylated and non-glycosylated substrates. *J Biol Chem,* 2012, 287, 36473-87.

[24] Reilley, K. J.; Giulianotti, M.; Dooley, C. T.; Nefzi, A.; McLaughlin, J. P. Houghten, R. A. Identification of two novel, potent, low-liability antinociceptive compounds from the direct in vivo screening of a large mixture-based combinatorial library. *The AAPS journal,* 2010, 12, 318-29.

[25] Wu, J.; Zhang, Y.; Maida, L. E.; Santos, R. G.; Welmaker, G. S.; LaVoi, T. M.; Nefzi, A.; Yu, Y.; Houghten, R. A., Toll, L. Giulianotti, M. A. Scaffold ranking and positional scanning utilized in the discovery of nAChR-selective compounds suitable for optimization studies. *J Med Chem,* 2013, 56, 10103-17.

[26] Mitchell, D. A.; Hamel, L. D.; Ishizuka, K.; Mitchell, G.; Schaefer, L. M. Deschenes, R. J. The Erf4 subunit of the yeast Ras palmitoyl acyltransferase is required for stability of the Acyl-Erf2 intermediate and palmitoyl transfer to a Ras2 substrate. *J Biol Chem,* 2012, 287, 34337-48.

[27] Mansilla, F.; Birkenkamp-Demtroder, K.; Kruhoffer, M.; Sorensen, F. B.; Andersen, C. L.; Laiho, P.; Aaltonen, L. A.; Verspaget, H. W. Orntoft, T. F. Differential expression of DHHC9 in microsatellite stable and instable human colorectal cancer subgroups. *British journal of cancer,* 2007, 96, 1896-903.

[28] Cuiffo, B. Ren, R. Palmitoylation of oncogenic NRAS is essential for leukemogenesis. *Blood,* 2010, 3598-3605.

[29] Choi, Y. W.; Bae, S. M.; Kim, Y. W.; Lee, H. N.; Park, T. C.; Ro, D. Y.; Shin, J. C.; Shin, S. J.; Seo, J. S. Ahn, W. S. Gene expression profiles in squamous cell cervical carcinoma using array-based comparative genomic hybridization analysis. *Int J Gynecol Cancer,* 2007, 17, 687-96.

[30] Oyama, T.; Miyoshi, Y.; Koyama, K.; Nakagawa, H.; Yamori, T.; Ito, T.; Matsuda, H.; Arakawa, H. Nakamura, Y. Isolation of a novel gene on 8p21.3-22 whose expression is reduced significantly in human colorectal cancers with liver metastasis. *Genes Chromosomes Cancer*, 2000, 29, 9-15.

[31] De Vos, M. L.; Lawrence, D. S. Smith, C. D. Cellular pharmacology of cerulenin analogs that inhibit protein palmitoylation. *Biochemical pharmacology*, 2001, 62, 985-95.

[32] Draper, J. M. Smith, C. D. Palmitoyl acyltransferase assays and inhibitors (Review). *Mol Membr Biol*, 2009, 26, 5-13.

[33] Planey, S. L. Zacharias, D. A. Identification of targets and inhibitors of protein palmitoylation. *Expert Opin Drug Discov*, 2010, 5, 155-64.

[34] Omura, S. The antibiotic cerulenin, a novel tool for biochemistry as an inhibitor of fatty acid synthesis. *Bacteriol Rev*, 1976, 40, 681-97.

[35] Patterson, S. I. Skene, J. H. Inhibition of dynamic protein palmitoylation in intact cells with tunicamycin. *Methods Enzymol*, 1995, 250, 284-300.

[36] Schlag, B. D.; Lou, Z.; Fennell, M. Dunlop, J. Ligand dependency of 5-hydroxytryptamine 2C receptor internalization. *J Pharmacol Exp Ther*, 2004, 310, 865-70.

[37] Christopher, J. A.; Brown, J.; Dore, A. S.; Errey, J. C.; Koglin, M.; Marshall, F. H.; Myszka, D. G.; Rich, R. L.; Tate, C. G.; Tehan, B.; Warne, T. Congreve, M. Biophysical fragment screening of the beta1-adrenergic receptor: identification of high affinity arylpiperazine leads using structure-based drug design. *J Med Chem*, 2013, 56, 3446-55.

[38] Debevec, G.; Chen, W.; Yu, Y.; Houghten, R. A. Giulianotti, M. A. Libraries from Libraries: A Series of Sulfonamide Linked Heterocycles Derived from the Same Scaffold. *Tetrahedron letters*, 2013, 54, 4296-4299.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A composition, comprising: a compound having the following structure:

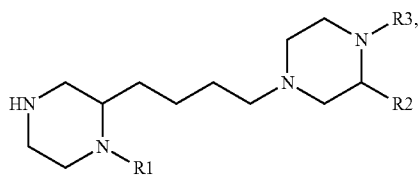

wherein each of R1, R2, and R3 is independently selected from the group consisting of:

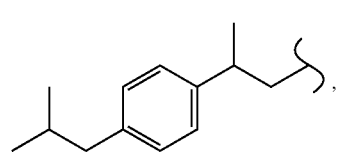

i.

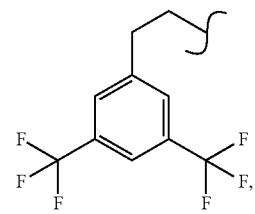

ii.

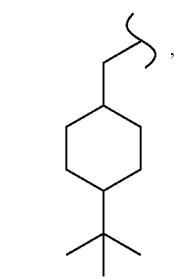

iii.

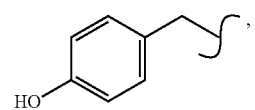

iv.

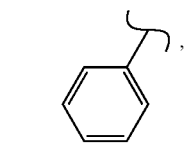

v.

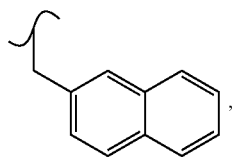

vi.

and vii.
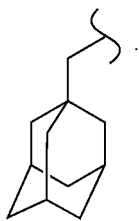
2. The composition of claim 1, wherein each of R1, R2, and R3 is independently selected from the group consisting of:
i.
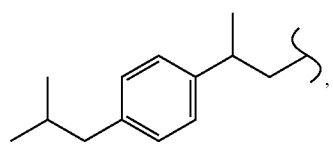
ii.
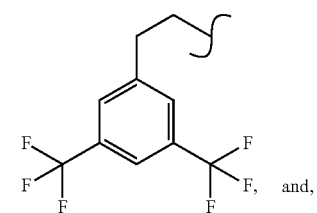  and,
iv.
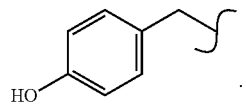
3. The composition of claim 1, wherein R1 is
i.
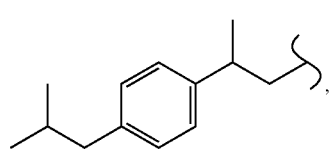
R2 is
iv.
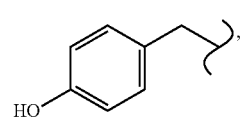
and R3 is
i.
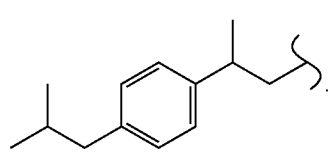
4. The composition of claim 1, wherein R1 is
i.
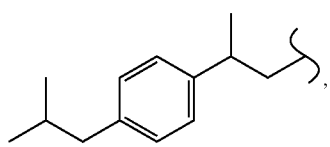
R2 is
iv.
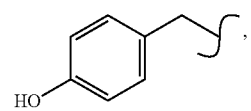
and R3 is
ii.
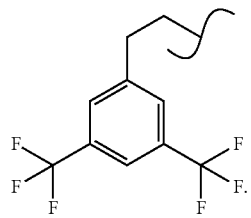
5. The composition of claim 1, wherein R1 is
ii.
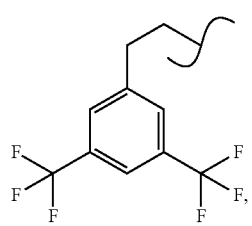
R2 is
iv.
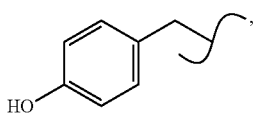
and R3 is
i.
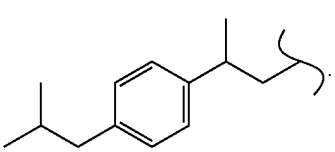

6. A pharmaceutical composition comprising a therapeutically effective amount of a compound or a pharmaceutically acceptable salt of the compound, and a pharmaceutically acceptable carrier, to treat a condition, wherein the compound has the following structure:

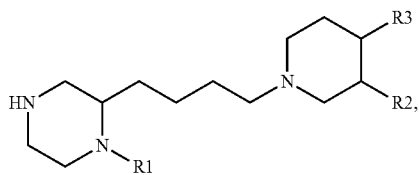

wherein each of R1, R2, and R3 is independently selected from the group consisting of:

i.
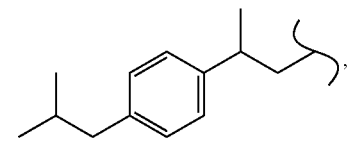

ii.
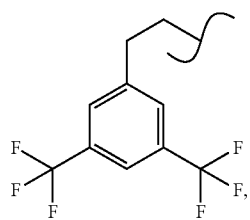

iii.
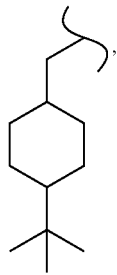

iv.
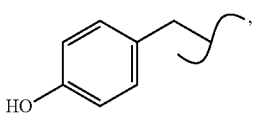

v.
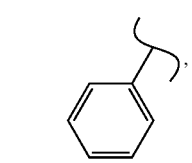

vi.
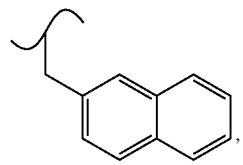

and vii.
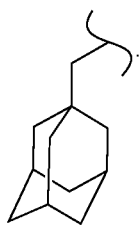

7. The pharmaceutical composition of claim 6, wherein the condition is a disease selected from the group consisting of: colorectal cancer, leukemia, and cervical cancer.

8. The pharmaceutical composition of claim 7, wherein each of R1, R2, and R3 is independently selected from the group consisting of:

i.

ii.

and, iv.

9. The pharmaceutical composition of claim 7, wherein R1 is i.

R2 is iv.

and R3 is

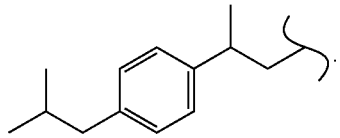

10. The pharmaceutical composition of claim 7, wherein R1 is

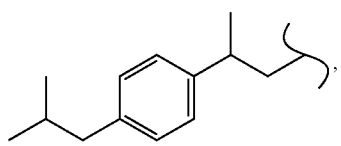

R2 is

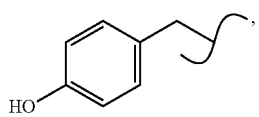

and R3 is

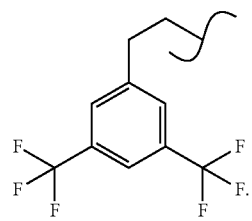

11. The pharmaceutical composition of claim 7, wherein R1 is

R2 is i.

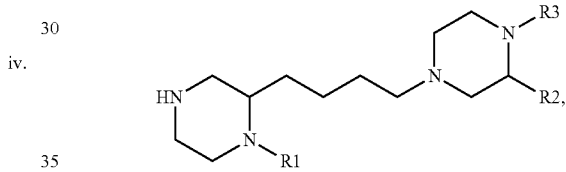

and R3 is i.

iv.

i.

12. A method of treating autopalmitoylation activity, comprising: delivering to a subject in need thereof, a pharmaceutical composition, wherein the pharmaceutical composition includes a therapeutically effective amount of a compound, or a pharmaceutically acceptable salt of the compound, and a pharmaceutically acceptable carrier, wherein the compound has the following structure:

wherein each of R1, R2, and R3 is independently selected from the group consisting of:

i.

ii.

iii.

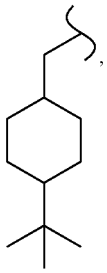

ii.

iv.
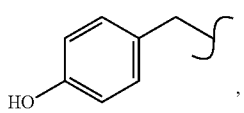,
v.
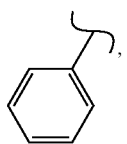,
vi.
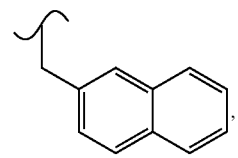,
and
vii.
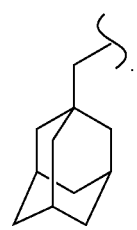.
13. The method of claim 12, wherein each of R1, R2, and R3 is independently selected from the group consisting of:
i.
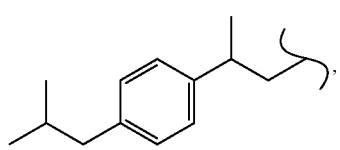,
ii.
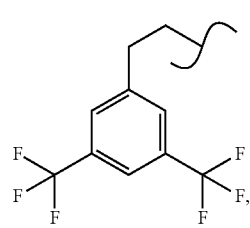,
and,
iv.
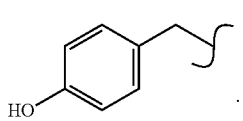.
14. The method of claim 12, wherein R1 is
i.
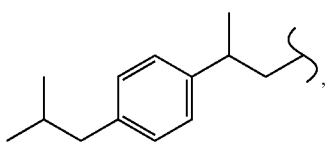,
R2 is
iv.
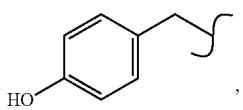,
and R3 is
i.
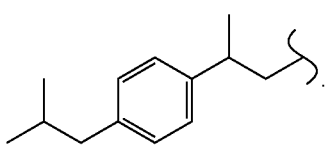.
15. The method of claim 12, wherein R1 is
i.
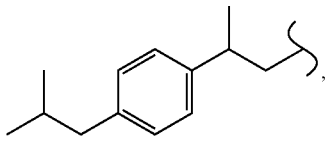,
R2 is
iv.
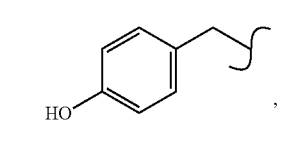,
and R3 is
ii.
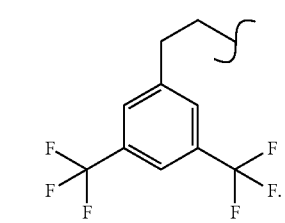.

16. The method of claim 12, wherein R1 is
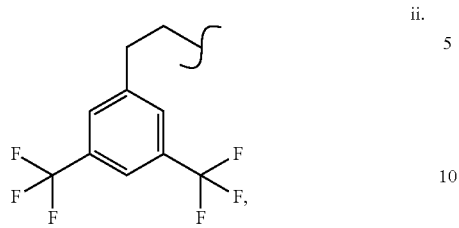
R2 is
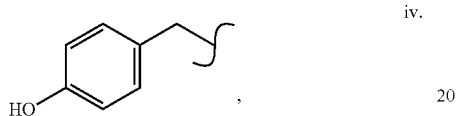
and R3 is
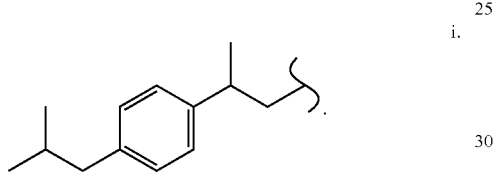
ii.
iv.
i.
* * * * *